(12) United States Patent  (10) Patent No.: US 9,409,882 B2
Anselm et al.  (45) Date of Patent: Aug. 9, 2016

(54) PYRIDINE DERIVATIVES

(71) Applicant: Hoffmann-La Roche Inc., Little Falls, NJ (US)

(72) Inventors: Lilli Anselm, Binzen (DE); David Banner, Basel (CH); Wolfgang Haap, Loerrach (DE); Bernd Kuhn, Reinach BL (CH); Thomas Luebbers, Loerrach (DE); Jens-Uwe Peters, Grenzach-Wyhlen (DE); Beat Spinnler, Rheinfelden (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/627,175

(22) Filed: Feb. 20, 2015

(65) Prior Publication Data

US 2015/0307472 A1   Oct. 29, 2015

Related U.S. Application Data

(63) Continuation of application No. PCT/EP2013/067218, filed on Aug. 19, 2013.

(30) Foreign Application Priority Data

Aug. 21, 2012 (EP) .................................... 12181247

(51) Int. Cl.
| | |
|---|---|
| *C07D 401/14* | (2006.01) |
| *C07D 401/08* | (2006.01) |
| *A61K 9/20* | (2006.01) |
| *A61K 9/48* | (2006.01) |

(52) U.S. Cl.
CPC ............ *C07D 401/08* (2013.01); *A61K 9/2054* (2013.01); *A61K 9/4858* (2013.01); *C07D 401/14* (2013.01)

(58) Field of Classification Search
CPC .................................................... A61K 9/2054
USPC .............................................. 546/256, 279.1
See application file for complete search history.

(56) References Cited

U.S. PATENT DOCUMENTS

| | | | |
|---|---|---|---|
| 8,394,834 B2 * | 3/2013 | Jablonski | C07D 413/14 514/318 |
| 8,969,386 B2 * | 3/2015 | Hadida-Ruah | C07D 213/75 514/333 |
| 2010/0267722 A1 | 10/2010 | Sanchez et al. | |

FOREIGN PATENT DOCUMENTS

| | | |
|---|---|---|
| WO | 01/25204 | 4/2001 |
| WO | 2006/073361 | 7/2006 |
| WO | 2007/086001 | 8/2007 |
| WO | 2009/068468 | 6/2009 |
| WO | 2009/109906 | 9/2009 |
| WO | 2010/121918 A1 | 10/2010 |
| WO | 2013/049559 | 4/2013 |

OTHER PUBLICATIONS

Hardegger et al., "Systematische Untersuchung von Halogenbrücken in Protein-Ligand-Wechselwirkungen", Angewandte Chemie 123:329-334 (2011).
English language explanation of Angew. Chem. 2011, 123, 329-334 (2011).
Supporting Information in English—Hardegger et al., "Systematic Investigation of Halogen Bonding in Protein-Ligand Interactions," pp. 1-145 (2010).

\* cited by examiner

*Primary Examiner* — Taofiq A. Solola

(57) ABSTRACT

The invention relates to a compound of formula (I)

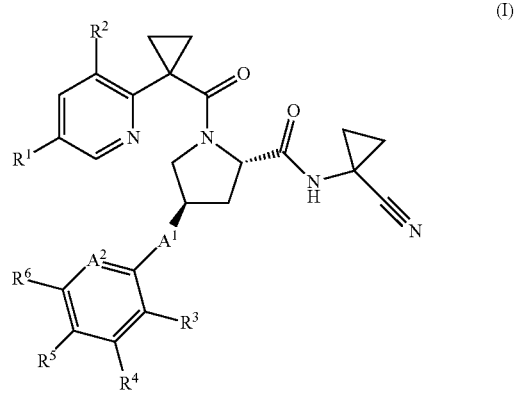

wherein $A^1$, $A^2$ and $R^1$ to $R^6$ are defined as in the description and in the claims. The compound of formula (I) can be used as a medicament.

17 Claims, No Drawings

PYRIDINE DERIVATIVES

CROSS REFERENCE TO RELATED APPLICATIONS

This Application is a continuation of International Application No. PCT/EP2013/067218 filed on Aug. 19, 2013, which is entitled to the priority of EP Application 12181247.3 filed on Aug. 21, 2012, the disclosures of which are incorporated herein by reference.

BACKGROUND OF THE INVENTION

Mammalian cathepsins are cysteine-type proteases involved in key steps of biological and pathological events. Cathepsins are considered tractable drug targets as it is feasible to inhibit enzymatic activity with small molecules and are therefore of interest to the pharmaceutical industry (Bromme, D. (2001), 'Papain-like cysteine proteases', Curr Protoc Protein Sci, Chapter 21, Unit 21 2; Roberts, R. (2005), 'Lysosomal cysteine proteases: structure, function and inhibition of cathepsins', Drug News Perspect, 18 (10), 605-14).

Cathepsin S is prominently expressed in antigen presenting cells like macrophages and dendritic cells and smooth muscle cells (Hsing, L. C. and Rudensky, A. Y. (2005), 'The lysosomal cysteine proteases in MHC class II antigen presentation', Immunol Rev, 207, 229-41; Rudensky, A. and Beers, C. (2006), 'Lysosomal cysteine proteases and antigen presentation', Ernst Schering Res Found Workshop, (56), 81-95). While Cathepsin S is only weakly expressed in normal arterial tissue, strong upregulation is seen in atherosclerotic arteries (Liu, J., et al. (2006), 'Increased serum cathepsin S in patients with atherosclerosis and diabetes', Atherosclerosis, 186 (2), 411-9; Sukhova, G. K., et al. (1998), 'Expression of the elastolytic cathepsins S and K in human atheroma and regulation of their production in smooth muscle cells', J Clin Invest, 102 (3), 576-83).

Preclinical data suggest that the function of Cathepsin S is critical for atherosclerosis as Cathepsin S deficient mice have a reduced atherosclerosis-phenotype when tested in appropriate mouse models. In LDL-Rec deficient mice reduced lipid accumulation, elastin-fibre breakdown and chronic arterial inflammation is reported. In APO E deficient mice a significant reduction of acute plaque rupture events was reported. When chronic renal disease is introduced into CatS/In APO-E deficient mice a strong reduction of accelerated calcification is seen on top of the anti atherosclerotic activity in arteries and heart valves Aikawa, E., et al. (2009), 'Arterial and aortic valve calcification abolished by elastolytic cathepsin S deficiency in chronic renal disease', Circulation, 119 (13), 1785-94; de Nooijer, R., et al. (2009), 'Leukocyte cathepsin S is a potent regulator of both cell and matrix turnover in advanced atherosclerosis', Arterioscler Thromb Vasc Biol, 29 (2), 188-94; Rodgers, K. J., et al. (2006), 'Destabilizing role of cathepsin S in murine atherosclerotic plaques', Arterioscler Thromb Vasc Biol, 26 (4), 851-6; Sukhova et al. (2003), 'Deficiency of cathepsin S reduces atherosclerosis in LDL receptor-deficient mice', J Clin Invest, 111 (6), 897-906). This suggests a potential inhibitor of Cathepsin S would stabilise atherosclerotic plaque by reducing extracellular matrix breakdown, by reducing the proinflammatory state and by reducing accelerated calcification and subsequently its clinical manifestations.

These phenotypes described in atherosclerosis models are in agreement with known cellular functions of Cathepsin S. Firstly, Cathepsin S is involved in the degradation of extracellular matrix that stabilises the plaque. In particular, Cathepsin S has potent elastinolytic activity and can exert this at neutral pH, a feature that distinguishes Cathepsin S from all other Cathepsins. Secondly, Cathepsin S is the major protease involved in antigen processing, in particular cleavage of the invariant chain in antigen presenting cells, resulting in reduced contribution of Tcells to the chronic inflammation of the atherosclerotic tissue. Elevated inflammation results in further oxidative and proteolytic tissue damage and subsequently plaque destabilisation (Cheng, X. W., et al. (2004), 'Increased expression of elastolytic cysteine proteases, cathepsins S and K, in the neointima of balloon-injured rat carotid arteries', Am J Pathol, 164 (1), 243-51; Driessen, C., et al. (1999), 'Cathepsin S controls the trafficking and maturation of MHC class II molecules in dendritic cells', J Cell Biol, 147 (4), 775-90; Rudensky, A. and Beers, C. (2006), 'Lysosomal cysteine proteases and antigen presentation', Ernst Schering Res Found Workshop, (56), 81-95).

The anti-inflammatory and anti-elastinolytic properties of a Cat S inhibitor make it also a prominent target for chronic obstructive pulmonary disease (Williams, A. S., et al. (2009), 'Role of cathepsin S in ozone-induced airway hyperresponsiveness and inflammation', Pulm Pharmacol Ther, 22 (1), 27-32). Furthermore due to its extracellular functions in matrix degradation, inhibition of cathepsin S will impact neointima formation and angiogenesis (Burns-Kurtis, C. L., et al. (2004), 'Cathepsin S expression is up-regulated following balloon angioplasty in the hypercholesterolemic rabbit', Cardiovasc Res, 62 (3), 610-20; Cheng, X. W., et al. (2004), 'Increased expression of elastolytic cysteine proteases, cathepsins S and K, in the neointima of balloon-injured rat carotid arteries', Am J Pathol, 164 (1), 243-51; Shi, G. P., et al. (2003), 'Deficiency of the cysteine protease cathepsin S impairs microvessel growth', Circ Res, 92 (5), 493-500; Wang, B., et al. (2006), 'Cathepsin S controls angiogenesis and tumor growth via matrix-derived angiogenic factors', J Biol Chem, 281 (9), 6020-9). An inhibitor of Cathepsin S might therefore be useful in several different disease settings.

Cathepsin S plays also a role in the reduction of tumor growth and tumor cell invasion as described by Roberta E. Burden in Clin Cancer Res 2009; 15(19). In addition, nephrectomized Cathepsin S knock out mice showed a significant reduction of arterial calcification when compared to nephrectomized wild type mice. This indicates that inhibition of Cathepsin S may have a beneficial effect on the reduction of cardiovascular events in chronic kidney disease patients (Elena Aikawa, Circulation, 2009, 1785-1794).

Cathepsin L shows a broader expression profile than cathepsin S and there are also data which suggest a role of cathepsin L in atherosclerosis, e.g. LDLrec & Cat L deficient mice show a reduced atherosclerotic phenotype (Kitamoto, S., et al. (2007), 'Cathepsin L deficiency reduces diet-induced atherosclerosis in low-density lipoprotein receptor-knockout mice', Circulation, 115 (15), 2065-75). In addition, Cat L was suggested to be involved in metabolic syndrome as it controls adipogenesis and peripheral glucose tolerance. In renal disease Cathepsin L is described to regulate podocyte function by proteolytically processing dynamin and thereby proteinuria (Sever, S., et al. (2007), 'Proteolytic processing of dynamin by cytoplasmic cathepsin L is a mechanism for proteinuric kidney disease', J Clin Invest, 117 (8), 2095-104).

Tissue remodelling, extracellular matrix degradation, the generation of active neuropeptides and roles in antigen presentation in thymic epithelial cells are cellular activities described for Cathepsin L (Funkelstein et al. (2008), (a) Major role of cathepsin L for producing the peptide hormones ACTH, β-Endorphin, and α-MSH, illustrated by protease gene knockout and expression, Journal of Biological Chemistry, 283(51), 35652-35659; (b) Cathepsin L participates in the production of neuropeptide Y in secretory vesicles, demonstrated by protease gene knockout and expression, Journal of Neurochemistry, 106(1), 384-391, Rudensky and Beers 2006).

SUMMARY OF THE INVENTION

The present invention relates to organic compounds useful for therapy and/or prophylaxis in a mammal, and in particular to compounds that are preferential inhibitors of the cysteine protease cathepsin, in particular of the cysteine protease cathepsin S or L.

The invention relates in particular to a compound of formula (I)

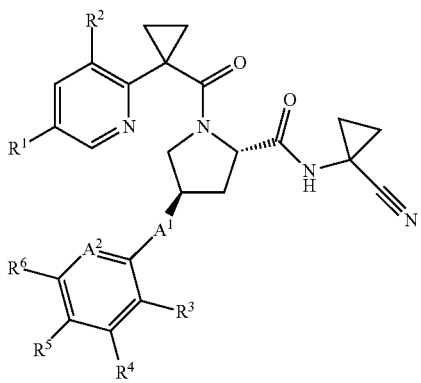

wherein
$A^1$ is —S— or —S(O)$_2$—;
$A^2$ is nitrogen or —(CH)—;
$R^1$ is halogen or haloalkyl;
$R^2$ is hydrogen or halogen;
$R^3$ is hydrogen, halogen, haloalkyl, pyrazolyl, [1,2,3]-triazolyl or [1,2,4]-triazolyl;
$R^4$ and $R^6$ are independently selected from hydrogen, alkyl, haloalkyl and halophenyl; and
$R^5$ is hydrogen, halogen, haloalkyl, alkoxy, haloalkoxy, alkylpyridinyl, halopyridinyl or alkylpyrazolyl;
or a pharmaceutically acceptable salt thereof.

The compounds of the invention are preferential inhibitors of the cysteine protease Cathepsin (Cat), in particular Cathepsin S or Cathepsin L and are therefore useful to treat metabolic diseases like diabetes, atherosclerosis, abdominal aortic aneurysm, peripheral arterial disease, cancer, reduction of cardiovascular events in chronic kidney disease, glomerulonephritis, age related macular degeneration, diabetic nephropathy and diabetic retinopathy. In addition, immune mediated diseases like rheumatoid arthritis, crohn's disease, multiple sclerosis, sjorgen syndrome, lupus erythematosus, neuropathic pain, diabetes type I, asthma and allergy and skin related immune disease are suitable diseases to be treated with a cathepsin S inhibitor.

Objects of the present invention are the compounds of formula (I) and their aforementioned salts per se and their use as therapeutically active substances, a process for the manufacture of the said compounds, intermediates, pharmaceutical compositions, medicaments containing the said compounds, their pharmaceutically acceptable salts, the use of the said compounds and salts for the prophylaxis and/or therapy of illnesses, especially in the treatment or prophylaxis of diabetes, atherosclerosis, abdominal aortic aneurysm, peripheral arterial disease, cancer, reduction of cardiovascular events in chronic kidney disease and diabetic nephropathy, and the use of the said compounds and salts for the production of medicaments for the treatment or prophylaxis of diabetes, atherosclerosis, abdominal aortic aneurysm, peripheral arterial disease, cancer, reduction of cardiovascular events in chronic kidney disease and diabetic nephropathy.

DETAILED DESCRIPTION OF THE INVENTION

In the present description the term "alkyl", alone or in combination, signifies a straight-chain or branched-chain alkyl group with 1 to 8 carbon atoms, in particular a straight or branched-chain alkyl group with 1 to 6 carbon atoms and particularly a straight or branched-chain alkyl group with 1 to 4 carbon atoms. Examples of straight-chain and branched C1-C8 alkyl groups are methyl, ethyl, propyl, isopropyl, butyl, isobutyl, tert.-butyl, the isomeric pentyls, the isomeric hexyls, the isomeric heptyls and the isomeric octyls, in particular methyl, ethyl, propyl, isopropyl, isobutyl and tert.-butyl, more particularly methyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec. butoxy and tert.butoxy, in particular methoxy.

The term "oxy", alone or in combination, signifies the —O— group.

The term "halogen" or "halo", alone or in combination, signifies fluorine, chlorine, bromine or iodine.

The terms "haloalkyl" and "haloalkoxy", alone or in combination, denote an alkyl group and an alkoxy group substituted with at least one halogen, in particular substituted with one to five halogens, particularly one to three halogens. A particular "haloalkyl" is trifluoromethyl. Particular haloalkoxy are trifluoroethoxy and trifluoropropyloxy.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, in particular, hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particular pharmaceutically acceptable salts of compound of formula (I) are the salts of hydrochloric acid, hydrobromic acid, sulfuric acid, phosphoric acid and methanesulfonic acid.

If one of the starting materials or compounds of formula (I) contains one or more functional groups which are not stable or are reactive under the reaction conditions of one or more reaction steps, appropriate protecting groups (as described e.g. in "Protective Groups in Organic Chemistry" by T. W. Greene and P. G. M. Wutts, 3rd Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The invention relates in particular to the following:

A compound of formula (I) wherein $A^1$ is —S(O)$_2$—;
A compound of formula (I) wherein $A^2$ is —(CH)—;
A compound of formula (I) wherein $R^1$ is chloro, bromo, iodo or trifluoromethyl;
A compound of formula (I) wherein $R^2$ is halogen;
A compound of formula (I) wherein $R^2$ is chloro or fluoro;
A compound of formula (I) wherein $R^3$ is hydrogen, halogen or haloalkyl;
A compound of formula (I) wherein $R^3$ is halogen;
A compound of formula (I) wherein $R^3$ is chloro;
A compound of formula (I) wherein $R^4$ and $R^6$ are independently selected from hydrogen and haloalkyl;
A compound of formula (I) wherein $R^4$ and $R^6$ are independently selected from hydrogen and trifluoromethyl;
A compound of formula (I) wherein $R^5$ is hydrogen, alkoxy, haloalkoxy, halogen, alkylpyridinyl or alkylpyrazolyl; and
A compound of formula (I) wherein $R^5$ is hydrogen, methoxy, trifluoroethoxy, fluoro, trifluoropropyloxy, bromo, methylpyridinyl or mehtylpyrazolyl.

The invention further relates to a compound of formula (I) selected from:

(2S,4R)-4-(2-Chloro-4-methoxy-benzenesulfonyl)-1-[1-(5-chloro-pyridin-2-yl)-cyclopropanecarbonyl]-pyrrolidine-2-carboxylic acid (1-cyano-cyclopropyl)-amide;

(2S,4R)-4-(2-Chloro-benzenesulfonyl)-1-[1-(5-chloro-pyridin-2-yl)-cyclopropanecarbonyl]-pyrrolidine-2-carboxylic acid (1-cyano-cyclopropyl)-amide;

(2S,4R)-1-[1-(5-Chloro-pyridin-2-yl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(2-chloro-4-methoxy-benzenesulfonyl)-pyrrolidine-2-carboxylic acid (1-cyano-cyclopropyl)-amide;

(2S,4R)-4-(2-Chloro-benzenesulfonyl)-1-[1-(5-chloro-3-fluoro-pyridin-2-yl)-cyclopropanecarbonyl]-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-1-[1-(5-Bromo-3-fluoro-pyridin-2-yl)-cyclopropanecarbonyl]-4-(2-chloro-4-methoxy-benzenesulfonyl)-pyrrolidine-2-carboxylic acid (1-cyano-cyclopropyl)-amide;

(2S,4R)-1-[1-(5-Bromo-3-fluoro-pyridin-2-yl)-cyclopropanecarbonyl]-4-(2-chloro-benzenesulfonyl)-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(4'-fluorobiphenyl-3-ylsulfanyl)-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(3-chloro-pyridin-2-ylsulfanyl)-pyrrolidine-2-carboxylic acid (1-cyano-cyclopropyl)-amide;

(2S,4R)-1-(1-(5-chloro-3-fluoropyridin-2-yl)cyclopropanecarbonyl)-4-(2-chloro-4-fluorophenylsulfonyl)-N-(1-cyanocyclopropyl)pyrrolidine-2-carboxamide;

(2S,4R)-1-[1-(5-Chloro-3-fluoro-pyridin-2-yl)-cyclopropanecarbonyl]-4-(pyridin-2-ylsulfanyl)-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(4'-fluorobiphenyl-3-sulfonyl)-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(3-chloropyridine-2-sulfonyl)-pyrrolidine-2-carboxylic acid (1-cyano-cyclopropyl)-amide;

(2S,4S)-4-(2-Chloro-4-fluoro-benzenesulfonyl)-1-[1-(5-chloro-3-fluoro-pyridin-2-yl)-cyclopropanecarbonyl]-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(3-chloro-5-trifluoromethyl-pyridin-2-ylsulfanyl)-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(5-chloro-pyridin-2-ylsulfanyl)-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(pyridine-2-sulfonyl)-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(6-methyl-pyridin-2-ylsulfanyl)-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(5-trifluoromethyl-pyridin-2-ylsulfanyl)-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(3-trifluoromethyl-pyridin-2-ylsulfanyl)-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(5-chloropyridine-2-sulfonyl)-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(6-methylpyridine-2-sulfonyl)-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(5-trifluoromethyl-pyridine-2-sulfonyl)-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(3-trifluoromethyl-pyridine-2-sulfonyl)-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(2-chloro-5-trifluoromethyl-phenylsulfanyl)-pyrrolidine-2-carboxylic acid (1-cyano-cyclopropyl)-amide;

(2S,4R)-1-(1-(5-chloro-3-fluoropyridin-2-yl)cyclopropanecarbonyl)-4-(2-chloro-4-((S)-1,1,1-trifluoropropan-2-yloxy)phenylsulfonyl)-N-(1-cyanocyclopropyl)pyrrolidine-2-carboxamide;

(2S,4R)-1-(1-(5-chloro-3-fluoropyridin-2-yl)cyclopropanecarbonyl)-4-(2-chloro-5-(trifluoromethyl)phenylsulfonyl)-N-(1-cyanocyclopropyl)pyrrolidine-2-carboxamide;

(2S,4R)-1-[1-(5-Chloro-pyridin-2-yl)-cyclopropanecarbonyl]-4-(2-chloro-5-trifluoromethyl-benzenesulfonyl)-pyrrolidine-2-carboxylic acid (1-cyano-cyclopropyl)-amide;

(2S,4R)-4-(4-Bromo-2-chloro-benzenesulfonyl)-1-[1-(5-chloro-3-fluoro-pyridin-2-yl)-cyclopropanecarbonyl]-pyrrolidine-2-carboxylic acid (1-cyano-cyclopropyl)-amide;

(2S,4R)-1-(1-(5-chloro-3-fluoropyridin-2-yl)cyclopropanecarbonyl)-4-(2-chloro-4-(2-methylpyridin-4-yl)phenylsulfonyl)-N-(1-cyanocyclopropyl)pyrrolidine-2-carboxamide;

(2S,4R)-4-[2-Chloro-4-(2-chloro-pyridin-4-yl)-benzenesulfonyl]-1-[1-(5-chloro-3-fluoro-pyridin-2-yl)-cyclopropanecarbonyl]-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-[2-chloro-4-(1-methyl-1H-pyrazol-4-yl)-benzenesulfonyl]-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-[2-chloro-4-(2-methyl-pyridin-3-yl)-benzenesulfonyl]-pyrrolidine-2-carboxylic acid (1-cyano-cyclopropyl)-amide;

(2S,4R)-4-[2-Chloro-4-(2-methyl-pyridin-3-yl)-benzenesulfonyl]-1-[1-(3-fluoro-5-trifluoromethyl-pyridin-2-yl)-cyclopropanecarbonyl]-pyrrolidine-2-carboxylic acid (1-cyano-cyclopropyl)-amide;

(2S,4R)-4-[2-Chloro-4-(2-methyl-pyridin-3-yl)-benzenesulfonyl]-1-[1-(3-fluoro-5-iodo-pyridin-2-yl)-cyclopropanecarbonyl]-pyrrolidine-2-carboxylic acid (1-cyano-cyclopropyl)-amide;

(2S,4R)-4-[2-Chloro-4-(2-methyl-pyridin-3-yl)-benzenesulfonyl]-1-[1-(3,5-dichloro-pyridin-2-yl)-cyclopropanecarbonyl]-pyrrolidine-2-carboxylic acid (1-cyano-cyclopropyl)-amide;

(2S,4R)-4-[2-Chloro-4-(1-methyl-1H-pyrazol-4-yl)-benzenesulfonyl]-1-[1-(3-fluoro-5-iodo-pyridin-2-yl)-cyclopropanecarbonyl]-pyrrolidine-2-carboxylic acid (1-cyano-cyclopropyl)-amide;

(2S,4R)-4-[2-Chloro-4-(1-methyl-1H-pyrazol-4-yl)-benzenesulfonyl]-1-[1-(3-fluoro-5-trifluoromethyl-pyridin-2-yl)-cyclopropanecarbonyl]-pyrrolidine-2-carboxylic acid (1-cyano-cyclopropyl)-amide;

(2S,4R)-4-[2-Chloro-4-(1-methyl-1H-pyrazol-4-yl)-benzenesulfonyl]-1-[1-(3,5-dichloro-pyridin-2-yl)-cyclopropanecarbonyl]-pyrrolidine-2-carboxylic acid (1-cyano-cyclopropyl)-amide;

(2S,4R)-4-(2-Fluoro-benzenesulfonyl)-1-[1-(3-fluoro-5-iodo-pyridin-2-yl)-cyclopropanecarbonyl]-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(2-fluoro-benzenesulfonyl)-pyrrolidine-2-carboxylic acid (1-cyano-cyclopropyl)-amide;

(2S,4R)-1-[1-(3-Fluoro-5-iodo-pyridin-2-yl)-cyclopropanecarbonyl]-4-(2-pyrazol-1-yl-benzenesulfonyl)-pyrrolidine-2-carboxylic acid (1-cyano-cyclopropyl)-amide;

(2S,4R)-1-[1-(3-Fluoro-5-iodo-pyridin-2-yl)-cyclopropanecarbonyl]-4-(2-[1,2,3]triazol-1-yl-benzenesulfonyl)-pyrrolidine-2-carboxylic acid (1-cyano-cyclopropyl)-amide;

(2S,4R)-1-[1-(3-Fluoro-5-iodo-pyridin-2-yl)-cyclopropanecarbonyl]-4-(2-[1,2,4]triazol-1-yl-benzenesulfonyl)-pyrrolidine-2-carboxylic acid (1-cyano-cyclopropyl)-amide;

((2S,4R)-1-[1-(5-Chloro-3-fluoro-pyridin-2-yl)-cyclopropanecarbonyl]-4-(2-pyrazol-1-yl-benzenesulfonyl)-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(2-[1,2,3]triazol-1-yl-benzenesulfonyl)-pyrrolidine-2-carboxylic acid (1-cyano-cyclopropyl)-amide; and (2S,4R)-1-[1-(5-Chloro-3-fluoro-pyridin-2-yl)-cyclopropanecarbonyl]-4-(2-[1,2,4]triazol-1-yl-benzenesulfonyl)-pyrrolidine-2-carboxylic acid (1-cyano-cyclopropyl)-amide.

The invention relates in particular to a compound of formula (I) selected from:

(2S,4R)-1-[1-(5-Chloro-3-fluoro-pyridin-2-yl)-cyclopropanecarbonyl]-4-(2-chloro-4-methoxy-benzenesulfonyl)-pyrrolidine-2-carboxylic acid (1-cyano-cyclopropyl)-amide;

(2S,4R)-4-(2-Chloro-benzenesulfonyl)-1-[1-(5-chloro-3-fluoro-pyridin-2-yl)-cyclopropanecarbonyl]-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-1-[1-(5-Bromo-3-fluoro-pyridin-2-yl)-cyclopropanecarbonyl]-4-(2-chloro-4-methoxy-benzenesulfonyl)-pyrrolidine-2-carboxylic acid (1-cyano-cyclopropyl)-amide;

(2S,4R)-1-[1-(5-Bromo-3-fluoro-pyridin-2-yl)-cyclopropanecarbonyl]-4-(2-chloro-benzenesulfonyl)-pyrrolidine-2-carboxylic acid (1-cyano-cyclopropyl)-amide;

(2S,4R)-1-(1-(5-chloro-3-fluoropyridin-2-yl)cyclopropanecarbonyl)-4-(2-chloro-4-fluorophenylsulfonyl)-N-(1-cyanocyclopropyl)pyrrolidine-2-carboxamide;

(2S,4R)-1-(1-(5-chloro-3-fluoropyridin-2-yl)cyclopropanecarbonyl)-4-(2-chloro-4-((S)-1,1,1-trifluoropropan-2-yloxy)phenylsulfonyl)-N-(1-cyanocyclopropyl)pyrrolidine-2-carboxamide;

(2S,4R)-1-(1-(5-chloro-3-fluoropyridin-2-yl)cyclopropanecarbonyl)-4-(2-chloro-5-(trifluoromethyl)phenylsulfonyl)-N-(1-cyanocyclopropyl)pyrrolidine-2-carboxamide;

(2S,4R)-4-(4-Bromo-2-chloro-benzenesulfonyl)-1-[1-(5-chloro-3-fluoro-pyridin-2-yl)-cyclopropanecarbonyl]-pyrrolidine-2-carboxylic acid (1-cyano-cyclopropyl)-amide;

(2S,4R)-1-(1-(5-chloro-3-fluoropyridin-2-yl)cyclopropanecarbonyl)-4-(2-chloro-4-(2-methylpyridin-4-yl)phenylsulfonyl)-N-(1-cyanocyclopropyl)pyrrolidine-2-carboxamide;

(2S,4R)-1-[1-(5-Chloro-3-fluoro-pyridin-2-yl)-cyclopropanecarbonyl]-4-[2-chloro-4-(1-methyl-1H-pyrazol-4-yl)-benzenesulfonyl]-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-[2-chloro-4-(2-methyl-pyridin-3-yl)-benzenesulfonyl]-pyrrolidine-2-carboxylic acid (1-cyano-cyclopropyl)-amide;

(2S,4R)-4-[2-Chloro-4-(2-methyl-pyridin-3-yl)-benzenesulfonyl]-1-[1-(3-fluoro-5-trifluoromethyl-pyridin-2-yl)-cyclopropanecarbonyl]-pyrrolidine-2-carboxylic acid (1-cyano-cyclopropyl)-amide;

(2S,4R)-4-[2-Chloro-4-(2-methyl-pyridin-3-yl)-benzenesulfonyl]-1-[1-(3-fluoro-5-iodo-pyridin-2-yl)-cyclopropanecarbonyl]-pyrrolidine-2-carboxylic acid (1-cyano-cyclopropyl)-amide;

(2S,4R)-4-[2-Chloro-4-(2-methyl-pyridin-3-yl)-benzenesulfonyl]-1-[1-(3,5-dichloro-pyridin-2-yl)-cyclopropanecarbonyl]-pyrrolidine-2-carboxylic acid (1-cyano-cyclopropyl)-amide;

(2S,4R)-4-[2-Chloro-4-(1-methyl-1H-pyrazol-4-yl)-benzenesulfonyl]-1-[1-(3-fluoro-5-iodo-pyridin-2-yl)-cyclopropanecarbonyl]-pyrrolidine-2-carboxylic acid (1-cyano-cyclopropyl)-amide;

(2S,4R)-4-[2-Chloro-4-(1-methyl-1H-pyrazol-4-yl)-benzenesulfonyl]-1-[1-(3-fluoro-5-trifluoromethyl-pyridin-2-yl)-cyclopropanecarbonyl]-pyrrolidine-2-carboxylic acid (1-cyano-cyclopropyl)-amide; and (2S,4R)-4-[2-Chloro-4-(1-methyl-1H-pyrazol-4-yl)-benzenesulfonyl]-1-[1-(3,5-dichloro-pyridin-2-yl)-cyclopropanecarbonyl]-pyrrolidine-2-carboxylic acid (1-cyano-cyclopropyl)-amide.

The compound of formula (I) can be prepared using procedures known in the art. The compound of formula (I) can also be prepared using the following procedures.

The following abbreviations are used in the present specification.

AcOEt: Ethyl acetate;
ACN: Acetonitrile;
boc: tert-Butyloxycarbonyl;
BOP: Benzotriazolyl-N-oxy-tris(dimethylamino)-phosphonium hexafluorophosphate;
BOP-Cl: Bis-(2-oxo-3-oxazolidinyl)-phosphinic acid chloride;
Cbz: Carbobenzyloxy;
CDI: 1,1'-Carbonyldiimidazole;
DCM: Dichloromethane;
DIEA: Diisopropyl ethyl amine;
DMAP: 4-Dimethylaminopyridine;
DMF: N,N-Dimethylformamide;
EDCI: N-(3-Dimetylaminopropyl)-N-ethyl-carbodiimide hydrochloride;
EtOAc: Ethyl acetate;
Fmoc: 9-Fluorenylmethyloxycarbonyl;
h: hour;
HATU: O-(7-azabenzotriazol-1-yl)-1,1,3,3-tetramethyluronium hexafluorophosphate;
HOBT: 1-Hydroxybenzotriazole;
Hunig's Base: Ethyl-diisopropyl-amine;
KHMDS: Potassium bis(trimethylsilyl)amide;
LDA: Lithiumdiisopropylamide;
LHMDS: Lithium bis(trimethylsilyl)amide;
mCPBA or MCPBA: meta-Chloroperoxybenzoic acid;
MeOH: Methanol;
Mes-Cl: Mesyl chloride;
min: minute;
Moz: Methoxybenzyl carbonyl;
$Na_2SO_4$: Sodium sulfate;
Nos-Cl: 3-Nitrobenzenesulfonyl chloride;
$Pd_2(dba)_3$: Tris(dibenzylideneacetone)dipalladium;
PyBOP: Benzotriazol-1-yl-oxytripyrrolidinephosphonium hexafluorophosphate;
TBTU: O-(Benzotriazol-1-yl)-N,N,N',N-tetramethyluronium terafluoroborate;
Teoc: Trimethylsilyl ethoxycarbonyl;
THF: Tetrahydrofurane;
TFA: Trifluoroacetic acid; and
Tos-Cl: Toluene-4-sulfonyl chloride.

Scheme 1

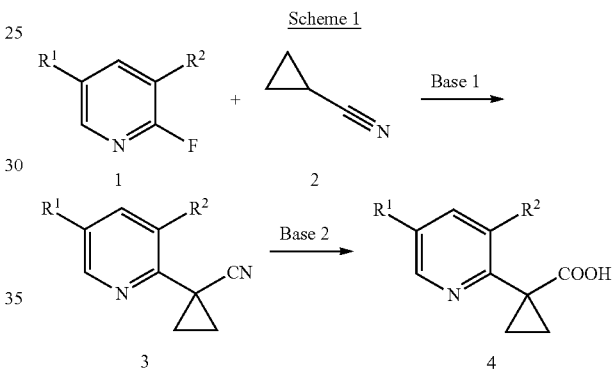

$R^1$-$R^2$ are as defined above; Base 1 is e.g. NaOtBu, KOtBu, NaH, LiHMDS, KHMDS or LDA; Base 2 is e.g. LiOH, NaOH or KOH.

A pyridine derivative such as 1 is treated with cyclopropanecarbonitrile 2 in the presence of a base (Base 1 as defined above) to yield the pyridine derivative 3. Compound 3 is treated with a base (Base 2 as defined above) to yield the final carboxylic acid derivative 4 as free acid or as a salt thereof.

Scheme 2

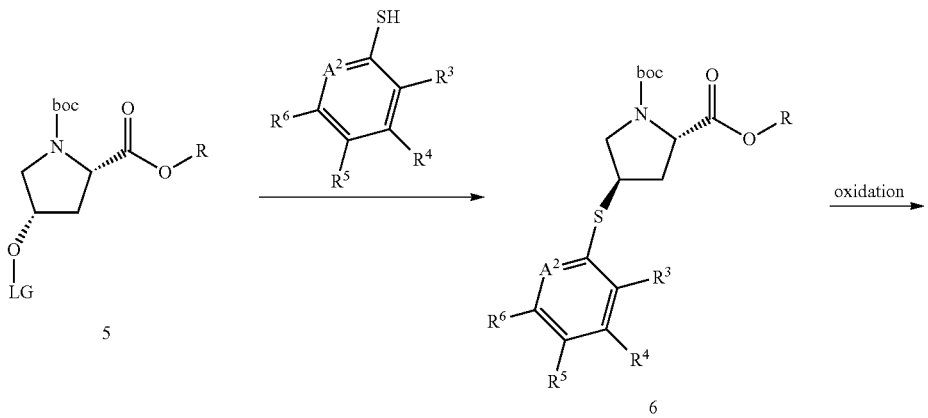

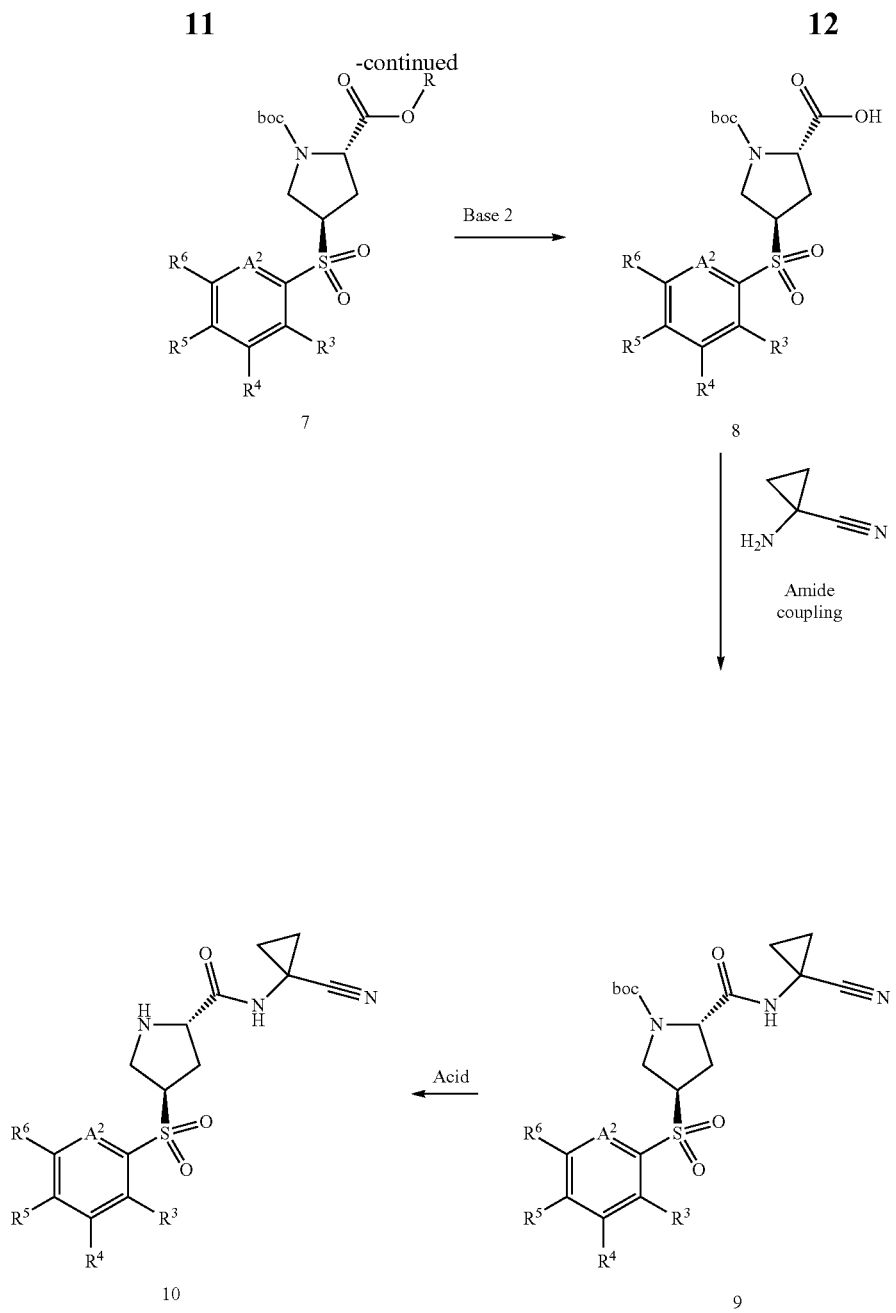

LG is a leaving group such as triflate, mesylate, tosylate, brosylate or nosylate; $A^2$ and $R^3$-$R^6$ are as defined above; R is e.g. Methyl, Ethyl, iPropyl or Benzyl.

A Boc-protected proline derivative 5 is reacted with a phenylthiol derivative in the presence of a base such as triethyl amine, DIEA, 2,6-lutidine, etc. to yield the thioether derivative 6. Oxidation of 6 with a peroxide reagent such as $H_2O_2$, oxone, mCPBA yields the sulfone derivative 7. Saponification of the ester to the acid with a base such as LiOH, NaOH or KOH yields the corresponding carboxylic acid 8 or salts thereof. Amide coupling is accomplished by reaction of 8 with 1-aminocarbonitrile derivative and a coupling reagent, such as EDCI, CDI, BOP-Cl, TBTU, HATU, PyBOP or BOP, in the presence of a base, such as DIEA, triethyl amine or lutidine, to yield amide 9. Finally, the Boc-protecting group is removed by treating compound 9 with an acid such as TFA, HCl in an organic solvent (e.g. AcOEt, dioxane) or formic acid to yield amine 10.

Scheme 3

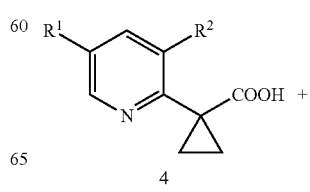

-continued

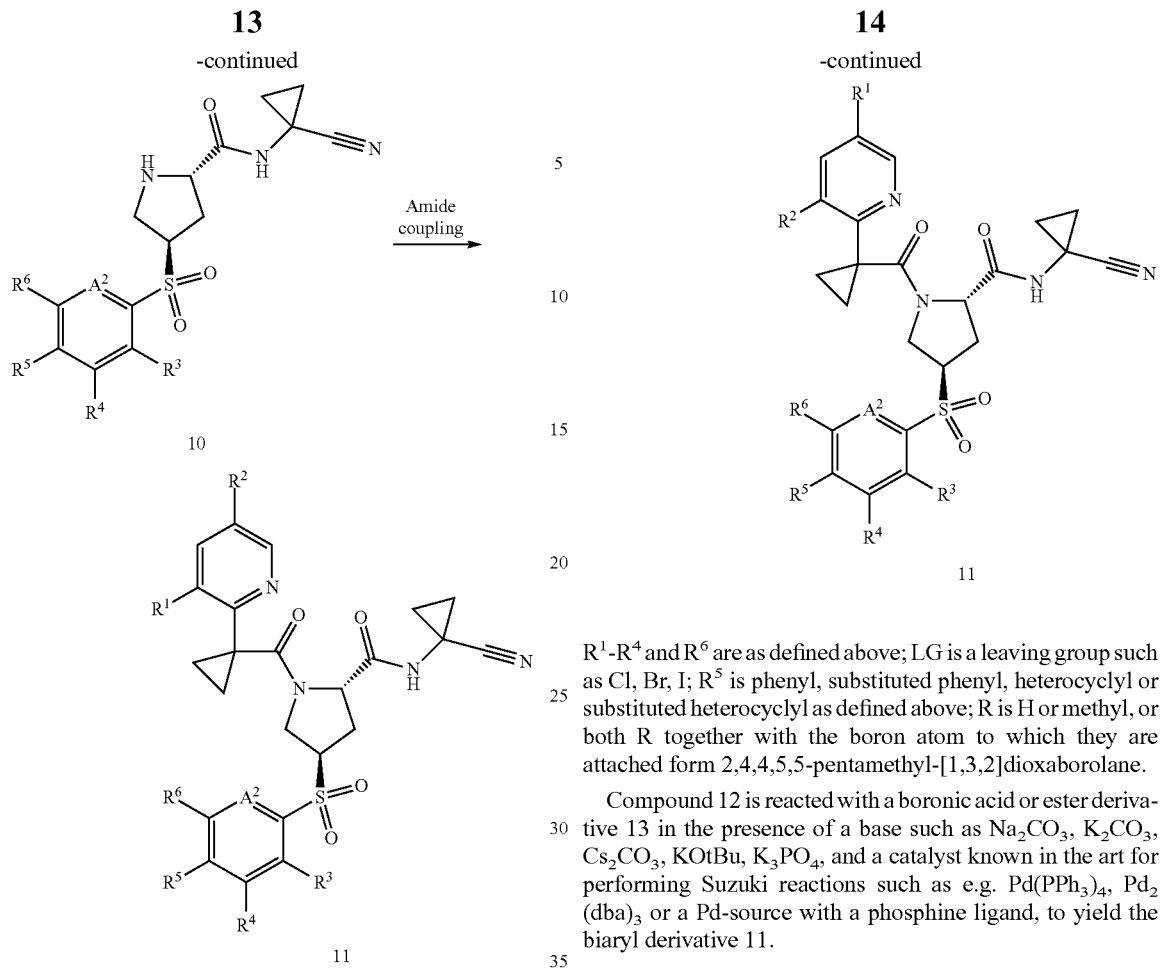

$R^1-R^4$ and $R^6$ are as defined above; LG is a leaving group such as Cl, Br, I; $R^5$ is phenyl, substituted phenyl, heterocyclyl or substituted heterocyclyl as defined above; R is H or methyl, or both R together with the boron atom to which they are attached form 2,4,4,5,5-pentamethyl-[1,3,2]dioxaborolane.

Compound 12 is reacted with a boronic acid or ester derivative 13 in the presence of a base such as $Na_2CO_3$, $K_2CO_3$, $Cs_2CO_3$, KOtBu, $K_3PO_4$, and a catalyst known in the art for performing Suzuki reactions such as e.g. $Pd(PPh_3)_4$, $Pd_2(dba)_3$ or a Pd-source with a phosphine ligand, to yield the biaryl derivative 11.

$A^2$ and $R^1-R^6$ are as defined above.

Carboxylic acid 4 is reacted with amine 10 in the presence of one of the amide coupling reagents, such as EDCI, CDI, BOP-Cl, TBTU, HATU, PyBOP or BOP, in the presence of a base such as DIEA, triethyl amine or 2,6-lutidine, to yield amide 11.

Scheme 4

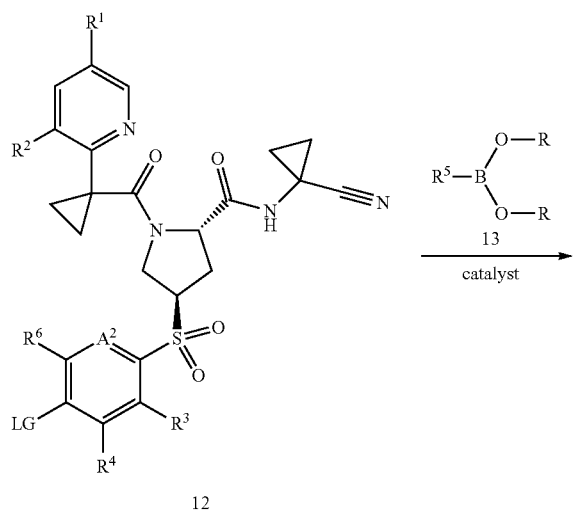

Scheme 5

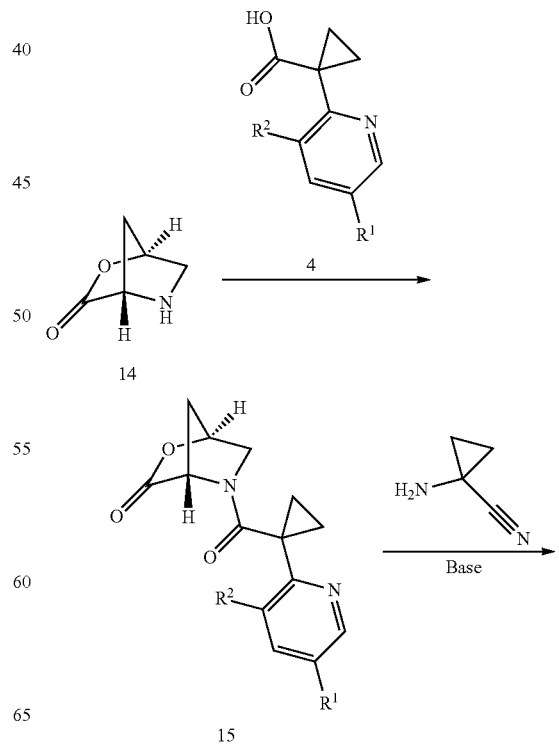

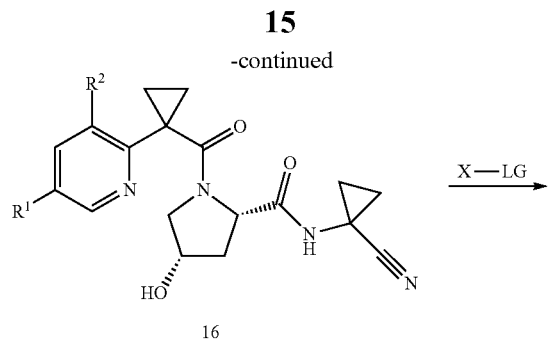

16

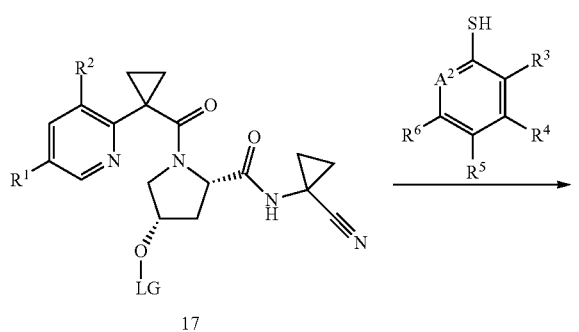

17

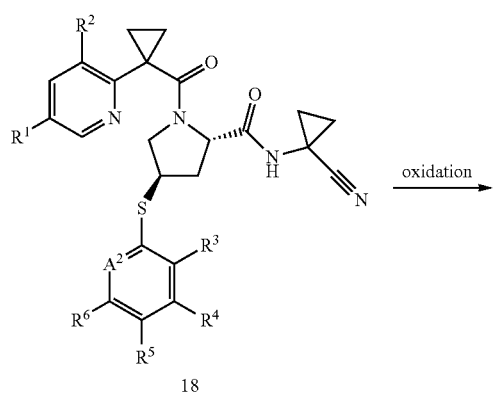

18 oxidation →

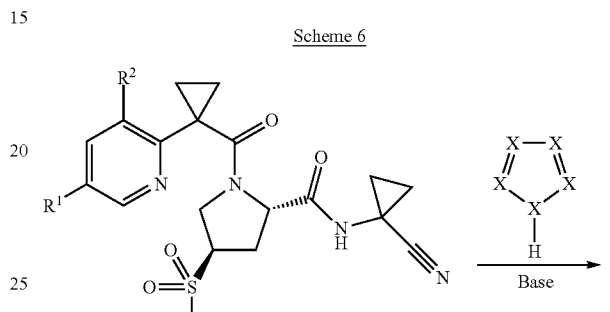

19

DIEA, triethyl amine, 2,6-lutidine, or alternatively, in the presence of an acid halogenide such as phosgene, triphosgene, oxalylchloride or thionylchloride, to yield amide 15. Opening of the lactone 15 by an amine is performed in the presence of an appropriate base such as sodium 2-ethylhexanoate, TEA, DIEA, DMAP, 2,6-lutidine or pyridine to yield the alcohol 16. Compound 16 is treated with X-LG in the presence of a base such as TEA, DIEA, DMAP, 2,6-lutidine or pyridine to yield the intermediate 17 which is subsequently reacted with thiols to yield the thioether 18. Oxidation of thioether 18 to the sulfone 19 is achieved by the reaction of 18 with oxidizing reagents such as $H_2O_2$, oxone, MCPBA.

Scheme 6

20

21

$R^3$ is a leaving group such as F, Cl, or $S(O)_2$-Me; X is either N or CH; Base is an inorganic base such as $Na_2CO_3$, $K_2CO_3$, $Cs_2CO_3$ or an organic base such as DIEA, triethylamine or 2,6-lutidine.

Compound 20 is dissolved in an appropriate solvent such as DMF, DMA or THF, a base as defined above and the nitrogen containing 5-membered heterocycle is added to the reaction mixture. The mixture is initially stirred at room temperature and subsequently heated to an elevated temperature from 30-100° C. until the reaction is completed.

The invention also relates to a process for the preparation of a compound of formula (I) as defined above, comprising one of the following steps:

LG is a leaving group such as triflate, mesylate, tosylate, brosylate or nosylate; $A^2$ and $R^1$-$R^6$ are as defined above; X is F, Cl, Br, I or X=O-LG.

The aminolactone 14 or a corresponding salt thereof such as hydrochloride, hydrobromide, phosphate, hydrogenphosphate, sulfate, hydrogensulfate, methansulfonate etc. is reacted with carboxylic acid 4 in the presence of an amide coupling reagent, such as EDCI, CDI, BOP-Cl, TBTU, HATU, PyBOP or BOP, in the presence of a base such as (a) The Reaction of a Compound of Formula (A)

(A)

in the presence of acid, wherein $A^1$, $A^2$ and $R^1$ to $R^6$ are as defined above and wherein PG is an amine protecting group;

(b) The Reaction of a Compound of Formula (B1)

(B1)

with a compound of formula (B2)

(B2)

in the presence of a base and an amide coupling agent and a base, wherein $A^1$, $A^2$ and $R^1$ to $R^6$ are as defined above;

(c) The Reaction of a Compound of Formula (C)

(C)

in the presence of $R^5B(OR)_2$, a base and a Suzuki catalyst, wherein $A^1$, $A^2$ and $R^1$ to $R^4$ and $R^6$ are as defined above, LG is a leaving group, $R^5$ is alkylpyridinyl, halopyridinyl or alkylpyrazolyl and R is hydrogen or methyl, or both R, together with the boron atom to which they are attached, form 2,4,4,5,5-pentamethyl-[1,3,2]dioxaborolane; or (d) The Reaction of a Compound of Formula (D)

(D)

in the presence of an oxidizing agent, wherein A and $R^1$ to $R^6$ are as defined above.

In step (a), the acid is for example TFA, HCl or formic acid.

In step (a), the amine protecting group is for example boc, Fmoc, Cbz, Teoc, benzyl or Moz.

In step (b), the amide coupling agent is for example EDCI, CDI, BOP-Cl, TBTU, HATU, PyBOP or BOP.

In step (b), the base is for example DIEA, triethyl amine or 2,6-lutidine.

In step (c), the leaving group is for example Cl, Br or I.

In step (c), the base is for example $Na_2CO_3$, $K_2CO_3$, $Cs_2CO_3$, KOtBu or $K_3PO_4$.

In step (c), the Suzuki catalyst is for example $Pd(PPh_3)_4$, $Pd_2(dba)_3$ or a Pd-source with a phosphine ligand.

In step (d), the oxidizing agent is for example $H_2O_2$, oxone or MCPBA.

A compound of formula (I), when manufactured according to the above process is also an object of the invention.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules are, for example, vegetable oils, waxes, fats, semi-solid substances and liquid polyols.

Suitable adjuvants for the production of solutions and syrups are, for example, water, polyols, saccharose, invert sugar and glucose.

Suitable adjuvants for injection solutions are, for example, water, alcohols, polyols, glycerol and vegetable oils.

Suitable adjuvants for suppositories are, for example, natural or hardened oils, waxes, fats, semi-solid and liquid polyols.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The invention thus also relates in particular to the following:

A compound of formula (I) for use as therapeutically active substance;

A pharmaceutical composition comprising a compound of formula (I) and a therapeutically inert carrier;

The use of a compound of formula (I) for the preparation of a medicament for the treatment or prophylaxis of diabetes, atherosclerosis, abdominal aortic aneurysm, peripheral arterial disease, cancer, reduction of cardiovascular events in chronic kidney disease, diabetic nephropathy, diabetic rethinopathy or age related macular degeneration;

A compound of formula (I) for the treatment or prophylaxis of diabetes, atherosclerosis, abdominal aortic aneurysm, peripheral arterial disease, cancer, reduction of cardiovascular events in chronic kidney disease, diabetic nephropathy, diabetic rethinopathy or age related macular degeneration; and A method for the treatment or prophylaxis of diabetes, atherosclerosis, abdominal aortic aneurysm, peripheral arterial disease, cancer, reduction of cardiovascular events in chronic kidney disease, diabetic nephropathy, diabetic rethinopathy or age related macular degeneration, which method comprises administering an effective amount of a compound of formula (I).

The invention will be illustrated by the following examples which have no limiting character.

EXAMPLES

Example 1

(2S,4R)-4-(2-Chloro-4-methoxy-benzenesulfonyl)-1-[1-(5-chloro-pyridin-2-yl)-cyclopropanecarbonyl]-pyrrolidine-2-carboxylic acid (1-cyano-cyclopropyl)-amide

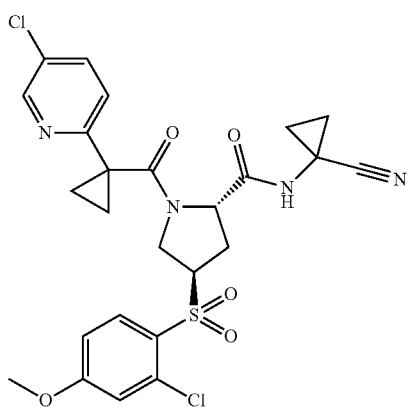 [SMILES: COc1ccc(S(=O)(=O)[C@@H]2C[C@@H](C(=O)NC3(C#N)CC3)N(C(=O)C3(c4ccc(Cl)cn4)CC3)C2)c(Cl)c1]

a)
1-(5-Chloro-pyridin-2-yl)-cyclopropanecarbonitrile

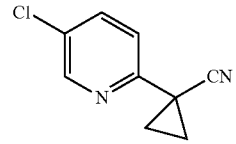 [SMILES: N#CC1(c2ccc(Cl)cn2)CC1]

To a solution of 5-chloro-2-fluoropyridine (2 g, 1.53 ml, 15.2 mmol, Eq: 1.00) and cyclopropanecarbonitrile (1.02 g, 1.15 ml, 15.2 mmol, Eq: 1.00) in toluene (20.0 ml) was added dropwise over 5 min. KHMDS 0.5 M in toluene (30.4 ml, 15.2 mmol, Eq: 1.00) at 0° C. The solution turned brown. After 45 min, the reaction mixture was allowed to warm up to 22° C. and stirred for 2.5 h. Saturated aqueous NH$_4$Cl solution (50 ml) was then added and the aqueous phase was extracted with AcOEt (3×60 ml). The combined organic phases were dried over Na$_2$SO$_4$, filtered and concentrated under reduced pressure. The crude material was purified by flash chromatography (silica gel, 70 g, 0% to 20% EtOAc in heptane) to yield the title compound as a white solid (840 mg; 31%). m/z=179.0373 [M+H]$^+$.

b) 1-(5-Chloro-pyridin-2-yl)-cyclopropanecarboxylic acid

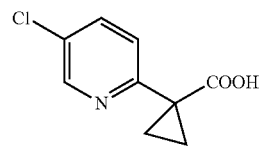 [SMILES: O=C(O)C1(c2ccc(Cl)cn2)CC1]

Compound 1a) (600 mg, 3.36 mmol, Eq: 1.00) was dissolved in 1% aqueous KOH solution (18 ml, 207 mg, 3.7 mmol, Eq: 1.1). The reaction mixture was stirred 17 h at 100° C. The crude reaction mixture was concentrated in vacuo and was acidified to pH 4. The crude material was purified by preparative HPLC to yield the title compound as a white solid (339 mg; 51%). m/z=198.1 [M+H]$^+$.

c) (2S,4R)-4-(2-Chloro-4-methoxy-benzenesulfonyl)-pyrrolidine-2-carboxylic acid (1-cyano-cyclopropyl)-amide HCl-salt

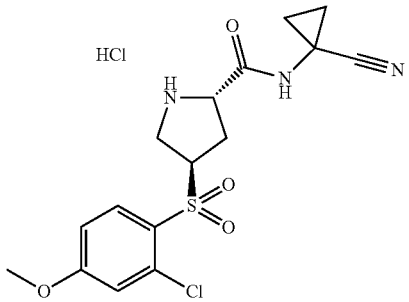 [SMILES: COc1ccc(S(=O)(=O)[C@H]2CN[C@H](C(=O)NC3(C#N)CC3)C2)c(Cl)c1 ; Cl]

CAS 1252640-17-7 (600 mg, 1.24 mmol, Eq: 1.00) was dissolved in HCl/dioxane (1.55 ml, 6.2 mmol, Eq: 5.00) and stirred at 22° C. for 4 h. The crude reaction mixture was concentrated in vacuo to yield a white solid (309 mg; 65%) which was used without further purification. m/z=384.2 [M+H]$^+$.

d) (2S,4R)-4-(2-Chloro-4-methoxy-benzenesulfonyl)-1-[1-(5-chloro-pyridin-2-yl)-cyclopropanecarbonyl]-pyrrolidine-2-carboxylic acid (1-cyano-cyclopropyl)-amide

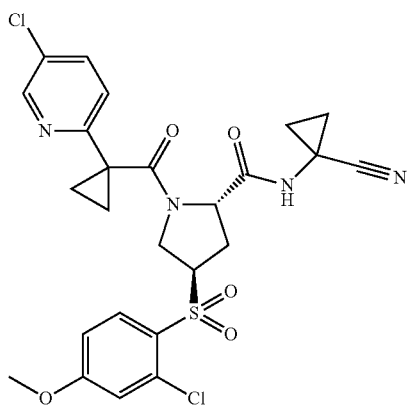 [SMILES: COc1ccc(S(=O)(=O)[C@@H]2C[C@@H](C(=O)NC3(C#N)CC3)N(C(=O)C3(c4ccc(Cl)cn4)CC3)C2)c(Cl)c1]

Example 1b) (61.8 mg, 313 µmol, Eq: 1.20) was dissolved in DMF (2 ml). HATU (198 mg, 521 µmol, Eq: 2.00), DIEA (67.3 mg, 91.0 µl, 521 µmol, Eq: 2.00) and example 1c) (100 mg, 261 µmol, Eq: 1.00) were added to the solution and stirred at 22° C. for 15 h. The crude material was purified by preparative HPLC to yield the title compound as a white solid (106 mg; 72%). m/z=563.2 [M+H]$^+$.

Example 2

(2S,4R)-4-(2-Chloro-benzenesulfonyl)-1-[1-(5-chloro-pyridin-2-yl)-cyclopropanecarbonyl]-pyrrolidine-2-carboxylic acid (1-cyano-cyclopropyl)-amide

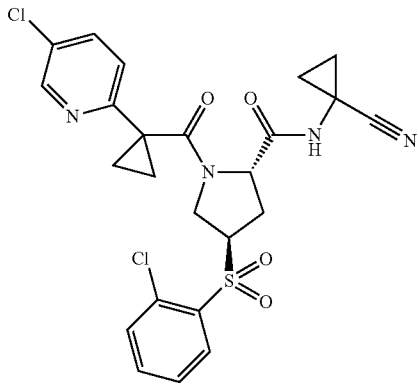 [SMILES: N#CC1(NC(=O)[C@@H]2C[C@@H](S(=O)(=O)c3ccccc3Cl)CN2C(=O)C2(c3ccc(Cl)cn3)CC2)CC1]

Example 2 was prepared in analogy to example 1 starting from CAS 1252638-10-0 to yield the title compound as a white solid (106 mg; 72%). m/z=533.2 [M+H]$^+$.

Example 3

(2S,4R)-1-[1-(5-Chloro-pyridin-2-yl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide

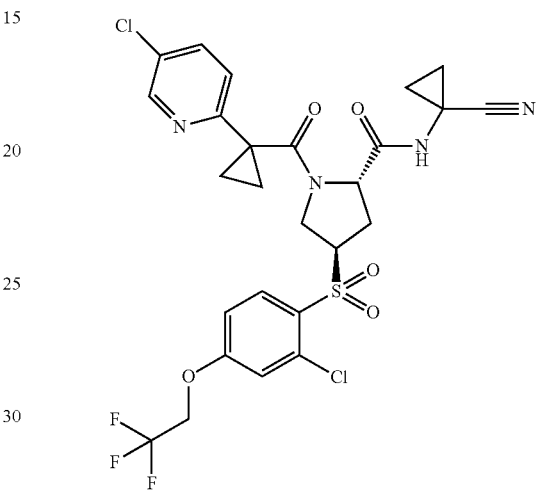

Example 3 was prepared in analogy to example 1 starting from CAS 1252634-04-0 to yield the title compound as a white solid (50 mg; 36%). m/z=631.1 [M+H]$^+$.

Example 4

(2S,4R)-1-[1-(5-Chloro-3-fluoro-pyridin-2-yl)-cyclopropanecarbonyl]-4-(2-chloro-4-methoxy-benzenesulfonyl)-pyrrolidine-2-carboxylic acid (1-cyano-cyclopropyl)-amide

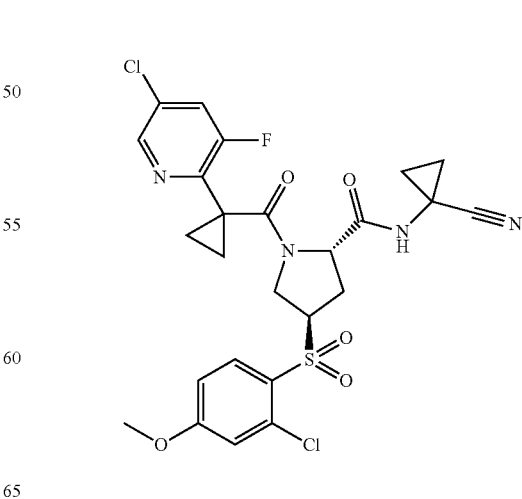

Example 4 was prepared in analogy to the methods described in example 1 starting from 5-chloro-2,3-difluoropyridine and example 1c) to yield the title compound as a white solid (45 mg; 30%). m/z=581.1 [M+H]⁺.

Example 5

(2S,4R)-4-(2-Chloro-benzenesulfonyl)-1-[1-(5-chloro-3-fluoro-pyridin-2-yl)-cyclopropanecarbonyl]-pyrrolidine-2-carboxylic acid (1-cyano-cyclopropyl)-amide

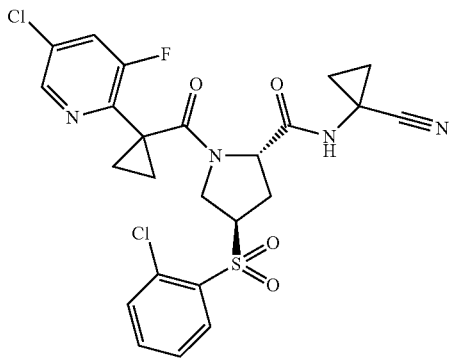 [SMILES: N#CC1(NC(=O)[C@@H]2C[C@@H](S(=O)(=O)c3ccccc3Cl)CN2C(=O)C2(c3ncc(Cl)cc3F)CC2)CC1]

Example 5 was prepared in analogy to the methods described in example 1 starting from 5-chloro-2,3-difluoropyridine and CAS 1252638-10-0 to yield the title compound as a white solid (99 mg; 64%). m/z=551.1 [M+H]⁺.

Example 6

(2S,4R)-1-[1-(5-Chloro-3-fluoro-pyridin-2-yl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide

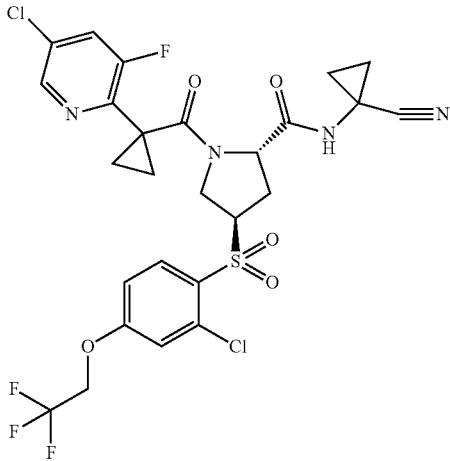 [SMILES: N#CC1(NC(=O)[C@@H]2C[C@@H](S(=O)(=O)c3ccc(OCC(F)(F)F)cc3Cl)CN2C(=O)C2(c3ncc(Cl)cc3F)CC2)CC1]

Example 6 was prepared in analogy to the methods described in example 1 starting from 5-chloro-2,3-difluoropyridine and CAS 1252634-04-0 to yield the title compound as a white solid (114 mg; 79%). m/z=649.2 [M+H]⁺.

Example 7

(2S,4R)-1-[1-(5-Bromo-3-fluoro-pyridin-2-yl)-cyclopropanecarbonyl]-4-(2-chloro-4-methoxy-benzenesulfonyl)-pyrrolidine-2-carboxylic acid (1-cyano-cyclopropyl)-amide

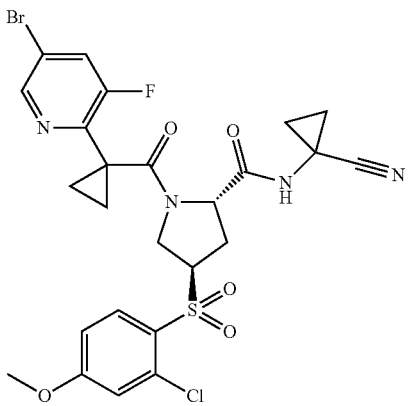

Example 7 was prepared in analogy to the methods described in example 1 starting from 5-bromo-2,3-difluoropyridine and example 1c) to yield the title compound as a white solid (14 mg; 17%). m/z=627.0 [M+H]⁺.

Example 8

(2S,4R)-1-[1-(5-Bromo-3-fluoro-pyridin-2-yl)-cyclopropanecarbonyl]-4-(2-chloro-benzenesulfonyl)-pyrrolidine-2-carboxylic acid (1-cyano-cyclopropyl)-amide

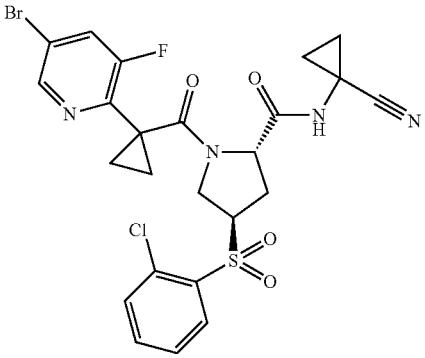 [SMILES: N#CC1(NC(=O)[C@@H]2C[C@@H](S(=O)(=O)c3ccccc3Cl)CN2C(=O)C2(c3ncc(Br)cc3F)CC2)CC1]

Example 8 was prepared in analogy to the methods described in example 1 starting from 5-bromo-2,3-difluoropyridine and CAS 1252638-10-0 to yield the title compound as a white foam (48 mg; 57%). m/z=597.0 [M+H]⁺.

Example 9

(2S,4R)-1-[1-(5-Chloro-3-fluoro-pyridin-2-yl)-cyclopropanecarbonyl]-4-(4'-fluorobiphenyl-3-ylsulfanyl)-pyrrolidine-2-carboxylic acid (1-cyano-cyclopropyl)-amide

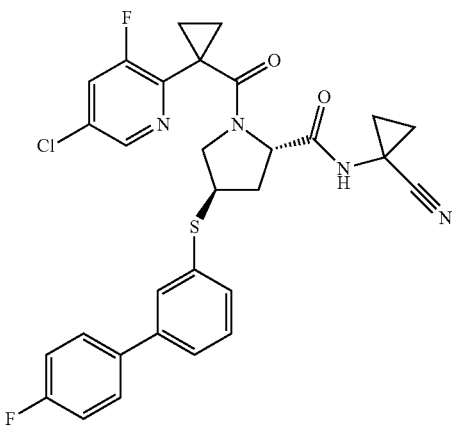 [SMILES: N#CC1(NC(=O)[C@@H]2C[C@@H](Sc3cccc(-c4ccc(F)cc4)c3)CN2C(=O)C2(c3ncc(Cl)cc3F)CC2)CC1]

a) (1S,4S)-5-[1-(5-Chloro-3-fluoro-pyridin-2-yl)-cyclopropanecarbonyl]-2-oxa-5-aza-bicyclo[2.2.1]heptan-3-one

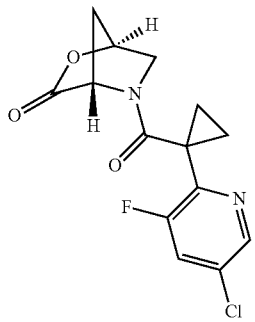 [SMILES: O=C1O[C@H]2C[C@@H]1N(C(=O)C1(c3ncc(Cl)cc3F)CC1)C2]

To a milky suspension of 5-chloro-3-fluoro-pyridine-2-carboxylic acid prepared in analogy of example 1b) (670 mg, 3.11 mmol, Eq: 1.00) in toluene (6 ml) at 25° C. was added DMF (11.4 mg, 12.0 µl, 155 µmol, Eq: 0.05). The mixture was cooled down to 0° C., then a solution of oxalyl chloride (434 mg, 299 µl, 3.42 mmol, Eq: 1.10) in toluene (2.00 ml) was dropped in within 10 min. The reaction mixture was stirred at 0° C. for 30 min, then without cooling for 3 h. At 0° C., (1S,4S)-2-oxa-5-aza-bicyclo[2.2.1]heptan-3-one methanesulfonate (CAS 769167-53-5) (650 mg, 3.11 mmol, Eq: 1.00) and THF (4.00 ml) were added to the reaction mixture, followed by TEA (1.18 g, 1.62 ml, 11.7 mmol, Eq: 3.75), dropped within 10 min (exothermic). The mixture was stirred at 22° C. for 16 h. The reaction mixture was poured into 20% aqueous citric acid solution (25 ml) and extracted with EtOAc (3×20 ml). The organic layers were dried over $Na_2SO_4$ and concentrated in vacuo. The crude material was purified by flash chromatography (silica gel, 40 g, 0% to 50% EtOAc in heptane) to yield the title compound as an orange oil (850 mg; 88%). m/z=311.1 $[M+H]^+$.

b) (2S,4S)-1-[1-(5-Chloro-3-fluoro-pyridin-2-yl)-cyclopropanecarbonyl]-4-hydroxy-pyrrolidine-2-carboxylic acid (1-cyano-cyclopropyl)-amide

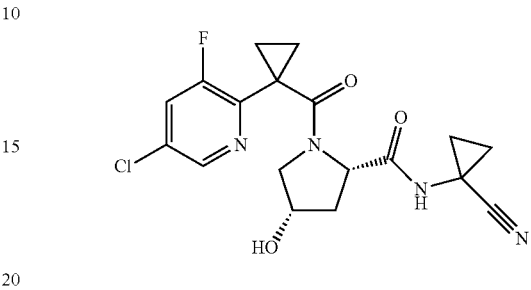

A mixture of example 9a) (850 mg, 2.74 mmol, Eq: 1.00), 1-aminocyclopropane-carbonitrile hydrochloride (422 mg, 3.56 mmol, Eq: 1.30), sodium 2-ethylhexanoate (705 mg, 4.24 mmol, Eq: 1.55) in water (3 ml) and THF (2.00 ml) was stirred at 55° C. for 18 h. To the reaction mixture were added hydrochloric acid (189 mg, 157 µl, 1.91 mmol, Eq: 0.70) and sodium chloride (1.36 g, 1.36 ml, 23.3 mmol, Eq: 8.50). The mixture was stirred for 15 min, then poured into AcOEt (25 ml) and extracted. The aqueous layer was back-extracted with AcOEt (3×20 ml). The organic layers were dried over $Na_2SO_4$ and concentrated in vacuo. The crude material was purified by flash chromatography (silica gel, 40 g, 0% to 90% EtOAc in heptane) to yield the title compound as white foam (560 mg; 52%). m/z=393.0 $[M+H]^+$.

c) 3-Nitro-benzenesulfonic acid (3S,5S)-1-[1-(5-chloro-3-fluoro-pyridin-2-yl)-cyclopropanecarbonyl]-5-(1-cyano-cyclopropylcarbamoyl)-pyrrolidin-3-yl ester

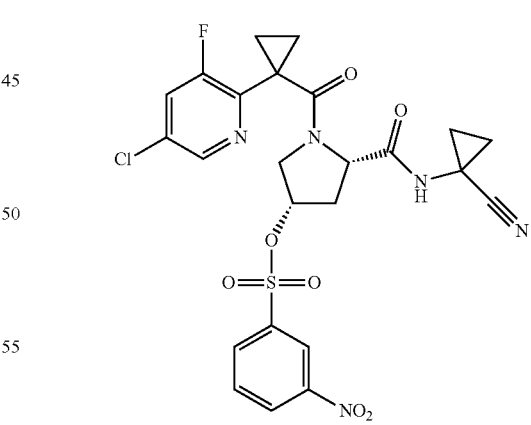

Example 9b) (560 mg, 1.43 mmol, Eq: 1.00) was dissolved in DCM (15 ml) and 3-nitrobenzene-1-sulfonyl chloride (335 mg, 1.51 mmol, Eq: 1.06) was added. The mixture was cooled down to 0° C. and TEA (433 mg, 596 µl, 4.28 mmol, Eq: 3.00) was slowly and carefully added with a syringe. The icebath was removed and the reaction mixture was stirred at 25° C. for 18 h. The reaction mixture was extracted with aqueous 10% $Na_2CO_3$ and 0.1 N aqueous HCl solutions. The organic layers were dried over Na$_2$SO$_4$, filtered and evaporated. The crude material was purified by flash chromatography (silica gel, 40 g, 0% to 85% EtOAc in heptane) to yield the title compound as off-white solid (510 mg; 62%). m/z=578.0 [M+H]$^+$.

d) (2S,4R)-1-[1-(5-Chloro-3-fluoro-pyridin-2-yl)-cyclopropanecarbonyl]-4-(4-fluorobiphenyl-3-ylsulfanyl)-pyrrolidine-2-carboxylic acid (1-cyano-cyclopropyl)-amide

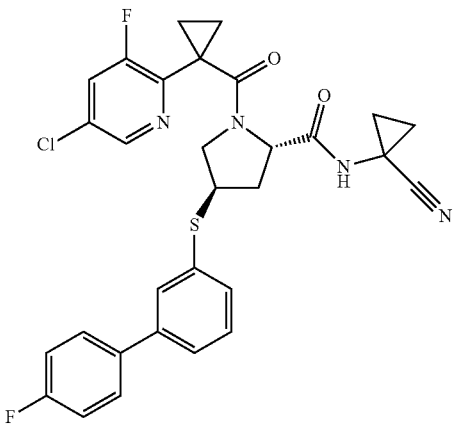 [SMILES: N#CC1(NC(=O)[C@@H]2C[C@@H](Sc3cccc(-c4ccc(F)cc4)c3)CN2C(=O)C2(c3ncc(Cl)cc3F)CC2)CC1]

Example 9c) (70 mg, 121 µmol, Eq: 1.00) and 4'-fluorobiphenyl-3-thiol (27.2 mg, 133 µmol, Eq: 1.10) were dissolved in propionitrile (1 ml). TEA (30.6 mg, 42.2 µl, 303 µmol, Eq: 2.50) was added and the reaction mixture was stirred at 90° C. for 3 h. The reaction mixture was poured into 0.1 M aqueous HCl solution (10 ml) and extracted with EtOAc (3×10 ml). The organic layers were combined, dried over Na$_2$SO$_4$ and concentrated in vacuo. The crude material was purified by flash chromatography (silica gel, 10 g, 0% to 66% EtOAc in heptane) to yield the title compound as off-white oil (46 mg; 68%). m/z=579.1 [M+H]$^+$.

Example 10

(2S,4R)-1-[1-(5-Chloro-3-fluoro-pyridin-2-yl)-cyclopropanecarbonyl]-4-(3-chloro-pyridin-2-ylsulfanyl)-pyrrolidine-2-carboxylic acid (1-cyano-cyclopropyl)-amide

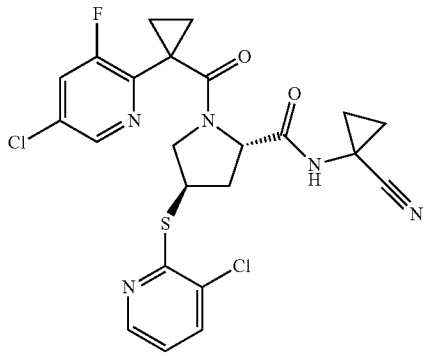 [SMILES: N#CC1(NC(=O)[C@@H]2C[C@@H](Sc3ncccc3Cl)CN2C(=O)C2(c3ncc(Cl)cc3F)CC2)CC1]

Example 10 was prepared in analogy to the methods described in example 9 starting from 3-chloropyridine-2-thiol and example 9c) to yield the title compound as a light yellow oil (50 mg; 79%). m/z=522.0 [M+H]$^+$.

Example 11

(2S,4R)-1-(1-(5-chloro-3-fluoropyridin-2-yl)cyclopropanecarbonyl)-4-(2-chloro-4-fluorophenylsulfonyl)-N-(1-cyanocyclopropyl)pyrrolidine-2-carboxamide

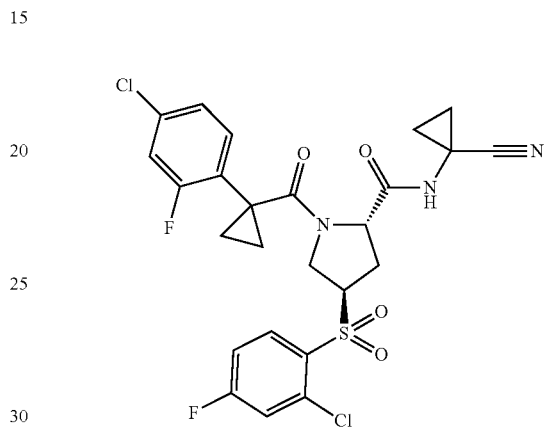

Example 11 was prepared in analogy to the methods described in example 1 starting from 5-chloro-2,3-difluoropyridine and CAS 1252633-65-0 to yield the title compound as a white solid (46 mg; 30%). m/z=569.0632 [M+H]$^+$.

Example 12

(2S,4R)-1-[1-(5-Chloro-3-fluoro-pyridin-2-yl)-cyclopropanecarbonyl]-4-(pyridin-2-ylsulfanyl)-pyrrolidine-2-carboxylic acid (1-cyano-cyclopropyl)-amide

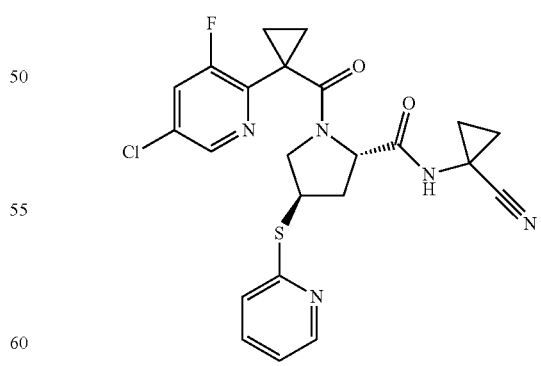

Example 12 was prepared in analogy to the methods described in example 9 starting from pyridine-2-thiol and example 9c) to yield the title compound as a colorless oil (4 mg; 7%). m/z=486.1 [M+H]$^+$.

Example 13

(2S,4R)-1-[1-(5-Chloro-3-fluoro-pyridin-2-yl)-cyclopropanecarbonyl]-4-(4'-fluorobiphenyl-3-sulfonyl)-pyrrolidine-2-carboxylic acid (1-cyano-cyclopropyl)-amide

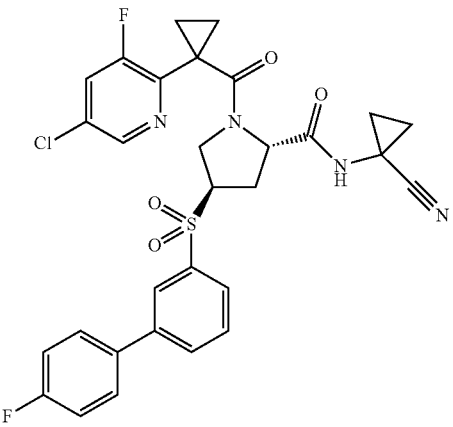 [SMILES: N#CC1(NC(=O)[C@@H]2C[C@@H](S(=O)(=O)c3cccc(-c4ccc(F)cc4)c3)CN2C(=O)C2(c3ncc(Cl)cc3F)CC2)CC1]

Example 9 (41 mg, 70.8 μmol, Eq: 1.00) was dissolved in DCM (1 ml) and mCPBA (25.7 mg, 149 μmol, Eq: 2.10) was added. The reaction mixture was stirred for 3 h at 22° C. The reaction mixture was poured into 10% aqueous $Na_2CO_3$ (5 ml) solution and extracted with DCM (3×5 ml). The organic layers were dried over $Na_2SO_4$, filtered and concentrated in vacuo to yield the title compound as a white solid (42 mg; 97%). m/z=611.0 [M+H]$^+$.

Example 14

(2S,4R)-1-[1-(5-Chloro-3-fluoro-pyridin-2-yl)-cyclopropanecarbonyl]-4-(3-chloropyridine-2-sulfonyl)-pyrrolidine-2-carboxylic acid (1-cyano-cyclopropyl)-amide

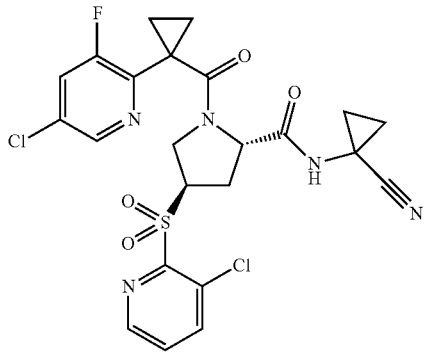 [SMILES: N#CC1(NC(=O)[C@@H]2C[C@@H](S(=O)(=O)c3ncccc3Cl)CN2C(=O)C2(c3ncc(Cl)cc3F)CC2)CC1]

Example 14 was prepared in analogy to the methods described in example 13 starting from example 10 to yield the title compound as a white solid (44 mg; 99%). m/z=552.1 [M+H]$^+$.

Example 15

(2S,4S)-4-(2-Chloro-4-fluoro-benzenesulfonyl)-1-[1-(5-chloro-3-fluoro-pyridin-2-yl)-cyclopropanecarbonyl]-pyrrolidine-2-carboxylic acid (1-cyano-cyclopropyl)-amide

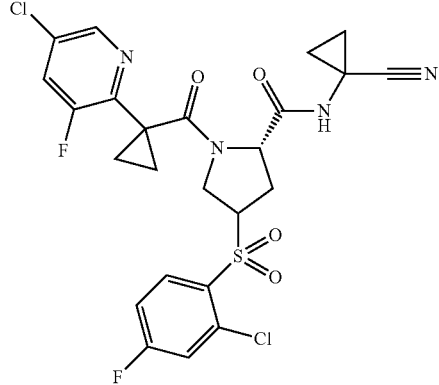 [SMILES: N#CC1(NC(=O)[C@@H]2CC(S(=O)(=O)c3ccc(F)cc3Cl)CN2C(=O)C2(c3ncc(Cl)cc3F)CC2)CC1]

Example 15 was obtained as a by-product during the synthesis of example 11 as light yellow solid (36 mg; 21%).

Example 16

(2S,4R)-1-[1-(5-Chloro-3-fluoro-pyridin-2-yl)-cyclopropanecarbonyl]-4-(3-chloro-5-trifluoromethyl-pyridin-2-ylsulfanyl)-pyrrolidine-2-carboxylic acid (1-cyano-cyclopropyl)-amide

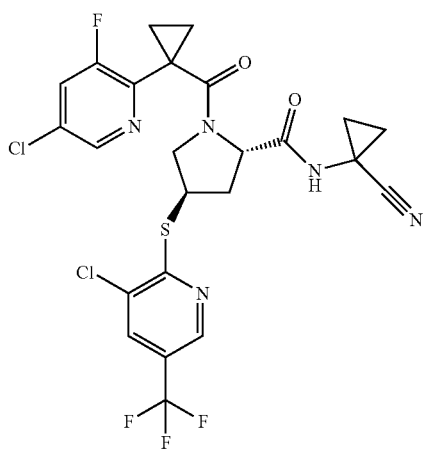 [SMILES: N#CC1(NC(=O)[C@@H]2C[C@@H](Sc3ncc(C(F)(F)F)cc3Cl)CN2C(=O)C2(c3ncc(Cl)cc3F)CC2)CC1]

Example 16 was prepared in analogy to the methods described in example 9 starting from 3-chloro-5-(trifluoromethyl)pyridine-2-thiol and example 9c) to yield the title compound as a light yellow oil (4 mg; 5%). m/z=585.9 [M+H]+.

Example 17

(2S,4R)-1-[1-(5-Chloro-3-fluoro-pyridin-2-yl)-cyclopropanecarbonyl]-4-(5-chloro-pyridin-2-ylsulfanyl)-pyrrolidine-2-carboxylic acid (1-cyano-cyclopropyl)-amide

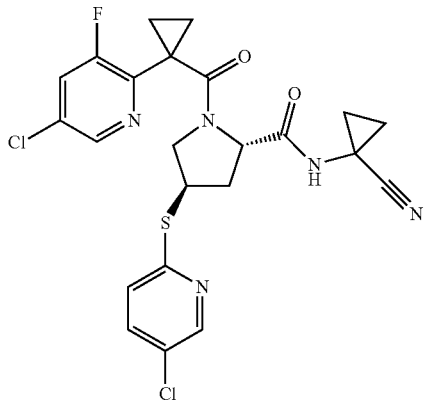 [SMILES: N#CC1(NC(=O)[C@@H]2C[C@@H](Sc3ccc(Cl)cn3)CN2C(=O)C2(c3ncc(Cl)cc3F)CC2)CC1]

Example 17 was prepared in analogy to the methods described in example 9 starting from 5-chloropyridine-2-thiol and example 9c) to yield the title compound as an off-white solid (30 mg; 83%). m/z=522.0 [M+H]+.

Example 18

(2S,4R)-1-[1-(5-Chloro-3-fluoro-pyridin-2-yl)-cyclopropanecarbonyl]-4-(pyridine-2-sulfonyl)-pyrrolidine-2-carboxylic acid (1-cyano-cyclopropyl)-amide

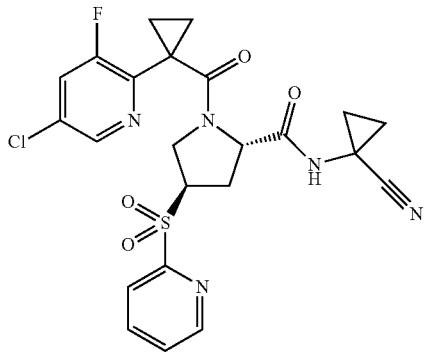 [SMILES: N#CC1(NC(=O)[C@@H]2C[C@@H](S(=O)(=O)c3ccccn3)CN2C(=O)C2(c3ncc(Cl)cc3F)CC2)CC1]

Example 18 was prepared in analogy to the methods described in example 13 starting from example 10 to yield the title compound as a off-white solid (3 mg; 94%). m/z=518.1 [M+H]+.

Example 19

(2S,4R)-1-[1-(5-Chloro-3-fluoro-pyridin-2-yl)-cyclopropanecarbonyl]-4-(6-methyl-pyridin-2-ylsulfanyl)-pyrrolidine-2-carboxylic acid (1-cyano-cyclopropyl)-amide

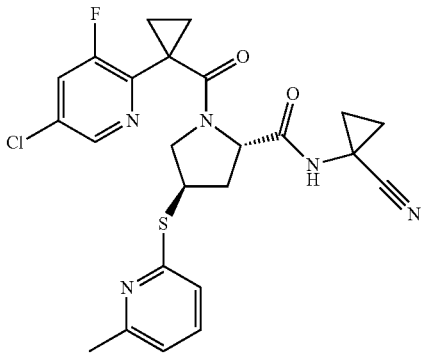 [SMILES: Cc1cccc(S[C@@H]2C[C@@H](C(=O)NC3(C#N)CC3)N(C(=O)C3(c4ncc(Cl)cc4F)CC3)C2)n1]

Example 19 was prepared in analogy to the methods described in example 9 starting from 6-methylpyridine-2-thiol and example 9c) to yield the title compound as an off-white solid (17 mg; 49%). m/z=500.1 [M+H]+.

Example 20

(2S,4R)-1-[1-(5-Chloro-3-fluoro-pyridin-2-yl)-cyclopropanecarbonyl]-4-(5-trifluoromethyl-pyridin-2-ylsulfanyl)-pyrrolidine-2-carboxylic acid (1-cyano-cyclopropyl)-amide

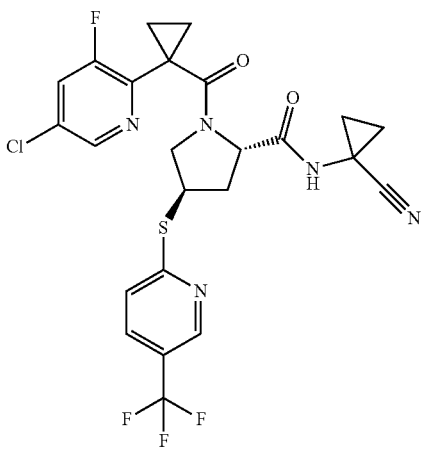 [SMILES: N#CC1(NC(=O)[C@@H]2C[C@@H](Sc3ccc(C(F)(F)F)cn3)CN2C(=O)C2(c3ncc(Cl)cc3F)CC2)CC1]

Example 20 was prepared in analogy to the methods described in example 9 starting from 5-(trifluoromethyl)pyridine-2-thiol and example 9c) to yield the title compound as a light yellow solid (32 mg; 84%). m/z=554.1 [M+H]+.

Example 21

(2S,4R)-1-[1-(5-Chloro-3-fluoro-pyridin-2-yl)-cyclo-propanecarbonyl]-4-(3-trifluoromethyl-pyridin-2-ylsulfanyl)-pyrrolidine-2-carboxylic acid (1-cyano-cyclopropyl)-amide

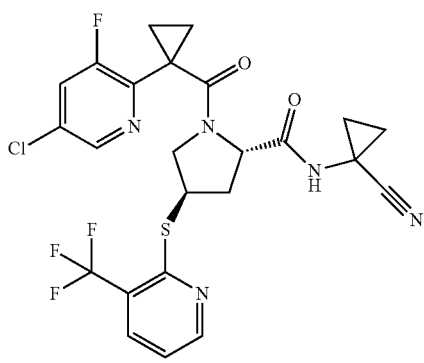 [SMILES: N#CC1(NC(=O)[C@@H]2C[C@@H](Sc3ncccc3C(F)(F)F)CN2C(=O)C2(c3ncc(Cl)cc3F)CC2)CC1]

Example 21 was prepared in analogy to the methods described in example 9 starting from 3-(trifluoromethyl)pyridine-2-thiol and example 9c) to yield the title compound as a yellow solid (33 mg; 86%). m/z=554.1 [M+H]$^+$.

Example 22

(2S,4R)-1-[1-(5-Chloro-3-fluoro-pyridin-2-yl)-cyclo-propanecarbonyl]-4-(5-chloropyridine-2-sulfonyl)-pyrrolidine-2-carboxylic acid (1-cyano-cyclopropyl)-amide

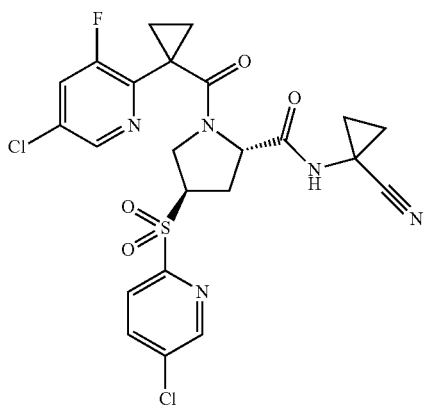 [SMILES: N#CC1(NC(=O)[C@@H]2C[C@@H](S(=O)(=O)c3ccc(Cl)cn3)CN2C(=O)C2(c3ncc(Cl)cc3F)CC2)CC1]

Example 22 was prepared in analogy to the methods described in example 13 starting from example 17 to yield the title compound as a white foam (22 mg; 80%). m/z=552.1 [M+H]$^+$.

Example 23

(2S,4R)-1-[1-(5-Chloro-3-fluoro-pyridin-2-yl)-cyclo-propanecarbonyl]-4-(6-methylpyridine-2-sulfonyl)-pyrrolidine-2-carboxylic acid (1-cyano-cyclopropyl)-amide

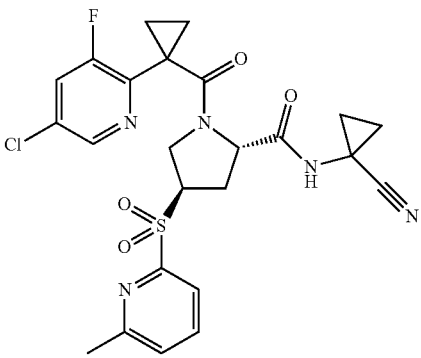 [SMILES: Cc1cccc(S(=O)(=O)[C@@H]2C[C@@H](C(=O)NC3(C#N)CC3)N(C(=O)C3(c4ncc(Cl)cc4F)CC3)C2)n1]

Example 23 was prepared in analogy to the methods described in example 13 starting from example 19 to yield the title compound as a white foam (13 mg; 82%). m/z=532.0 [M+H]$^+$.

Example 24

(2S,4R)-1-[1-(5-Chloro-3-fluoro-pyridin-2-yl)-cyclo-propanecarbonyl]-4-(5-trifluoromethyl-pyridine-2-sulfonyl)-pyrrolidine-2-carboxylic acid (1-cyano-cyclopropyl)-amide

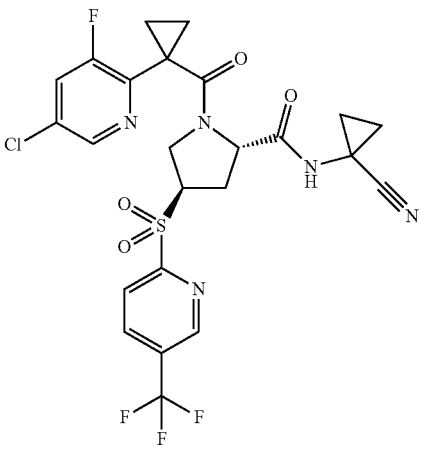 [SMILES: N#CC1(NC(=O)[C@@H]2C[C@@H](S(=O)(=O)c3ccc(C(F)(F)F)cn3)CN2C(=O)C2(c3ncc(Cl)cc3F)CC2)CC1]

Example 24 was prepared in analogy to the methods described in example 13 starting from example 20 to yield the title compound as a white solid (29 mg; 98%). m/z=585.9 [M+H]$^+$.

Example 25

(2S,4R)-1-[1-(5-Chloro-3-fluoro-pyridin-2-yl)-cyclopropanecarbonyl]-4-(3-trifluoromethyl-pyridine-2-sulfonyl)-pyrrolidine-2-carboxylic acid (1-cyano-cyclopropyl)-amide

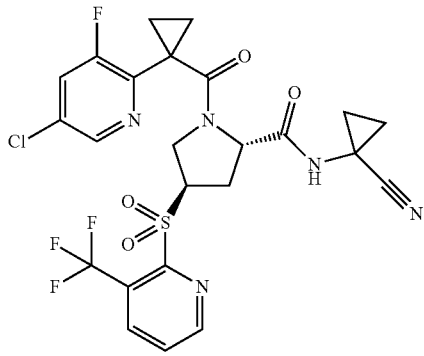 [SMILES: N#CC1(NC(=O)[C@@H]2C[C@@H](S(=O)(=O)c3ncccc3C(F)(F)F)CN2C(=O)C2(c3ncc(Cl)cc3F)CC2)CC1]

Example 25 was prepared in analogy to the methods described in example 13 starting from example 21 to yield the title compound as a white solid (16 mg; 52%). m/z=585.9 [M+H]$^+$.

Example 26

(2S,4R)-1-[1-(5-Chloro-3-fluoro-pyridin-2-yl)-cyclopropanecarbonyl]-4-(2-chloro-5-trifluoromethyl-phenylsulfanyl)-pyrrolidine-2-carboxylic acid (1-cyano-cyclopropyl)-amide

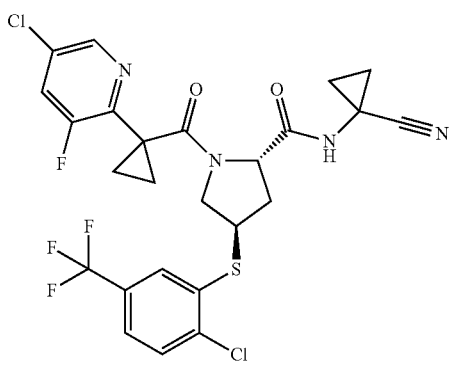 [SMILES: N#CC1(NC(=O)[C@@H]2C[C@@H](Sc3cc(C(F)(F)F)ccc3Cl)CN2C(=O)C2(c3ncc(Cl)cc3F)CC2)CC1]

Example 26 was prepared in analogy to the methods described in example 9 starting from 2-chloro-5-(trifluoromethyl)benzenethiol and example 9c) to yield the title compound as a white solid (10 mg; 25%). m/z=586.9 [M+H]$^+$.

Example 27

(2S,4R)-1-(1-(5-chloro-3-fluoropyridin-2-yl)cyclopropanecarbonyl)-4-(2-chloro-4-((S)-1,1,1-trifluoropropan-2-yloxy)phenylsulfonyl)-N-(1-cyanocyclopropyl)pyrrolidine-2-carboxamide

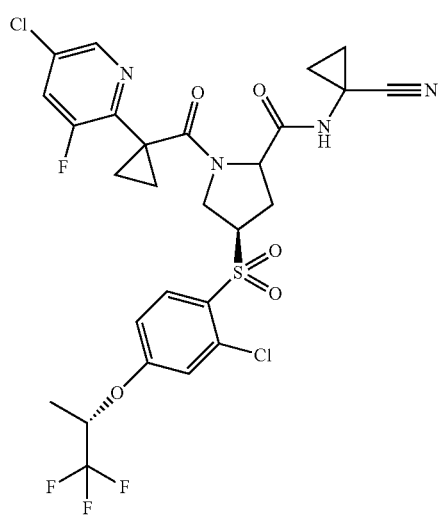 [SMILES: C[C@H](Oc1ccc(S(=O)(=O)[C@@H]2CC(C(=O)NC3(C#N)CC3)N(C(=O)C3(c4ncc(Cl)cc4F)CC3)C2)c(Cl)c1)C(F)(F)F]

Example 11 (27 mg, 47.4 µmol, Eq: 1.00) was dissolved in DMF (1 ml). Cs$_2$CO$_3$ (23.2 mg, 71.1 µmol, Eq: 1.50) and (S)-1,1,1-trifluoropropan-2-ol (5.95 mg, 52.2 µmol, Eq: 1.10) were added to the solution and stirred at 40° C. for 4 h. The crude material was purified by preparative HPLC to yield the title compound as a white solid (17 mg; 54%). m/z=663.2 [M+H]$^+$.

Example 28

(2S,4R)-1-(1-(5-chloro-3-fluoropyridin-2-yl)cyclopropanecarbonyl)-4-(2-chloro-5-(trifluoromethyl)phenylsulfonyl)-N-(1-cyanocyclopropyl)pyrrolidine-2-carboxamide

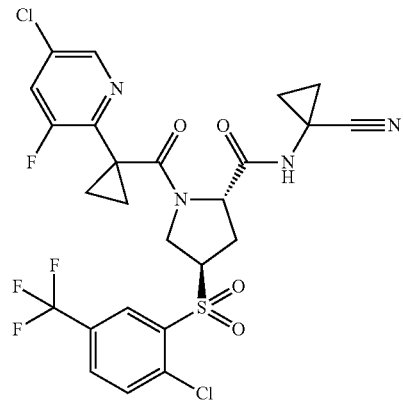 [SMILES: N#CC1(NC(=O)[C@@H]2C[C@@H](S(=O)(=O)c3cc(C(F)(F)F)ccc3Cl)CN2C(=O)C2(c3ncc(Cl)cc3F)CC2)CC1]

a) (2S,4R)-4-(2-Chloro-5-trifluoromethyl-benzene-sulfonyl)-pyrrolidine-2-carboxylicacid (1-cyano-cyclopropyl)-amide

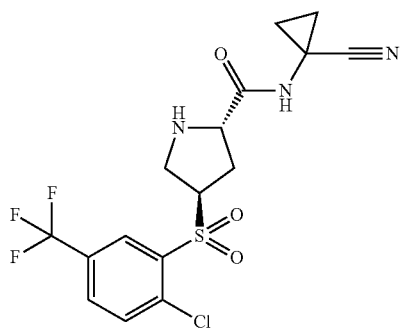 [SMILES: N#CC1(NC(=O)[C@@H]2C[C@@H](S(=O)(=O)c3cc(C(F)(F)F)ccc3Cl)CN2)CC1]

Example 28a) was prepared in analogy to the methods described for CAS 1252638-10-0 (see Haap et al.; US20100267722 and Hardegger et al.; Angewandte Chemie, International Edition, 50(1), 314-318, S314/1-S314/145; 2011) starting from 2-chloro-5-triflurormethyl-benzenethiol to yield the title compound as a light yellow solid (125 mg; 74%)) mz=421.9 [M+H]+$^{+}$.

b) (2S,4R)-1-(1-(5-chloro-3-fluoropyridin-2-yl)cyclopropanecarbonyl)-4-(2-chloro-5-(trifluoromethyl)phenylsulfonyl)-N-(1-cyanocyclopropyl)pyrrolidine-2-carboxamide

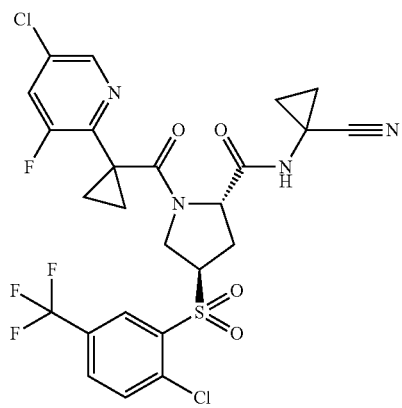 [SMILES: N#CC1(NC(=O)[C@@H]2C[C@@H](S(=O)(=O)c3cc(C(F)(F)F)ccc3Cl)CN2C(=O)C2(c3ncc(Cl)cc3F)CC2)CC1]

Example 28b) was prepared in analogy to example 1 strating from example 28a) and 5-chloro-2,3-difluoropyridine to yield the title compound as a white solid (37 mg; 50%). m/z=619.1 [M+H]$^{+}$.

Example 29

(2S,4R)-1-[1-(5-Chloro-pyridin-2-yl)-cyclopropanecarbonyl]-4-(2-chloro-5-trifluoromethyl-benzene-sulfonyl)-pyrrolidine-2-carboxylic acid (1-cyano-cyclopropyl)-amide

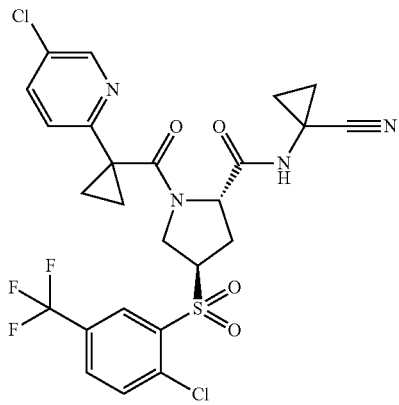 [SMILES: N#CC1(NC(=O)[C@@H]2C[C@@H](S(=O)(=O)c3cc(C(F)(F)F)ccc3Cl)CN2C(=O)C2(c3ccc(Cl)cn3)CC2)CC1]

Example 29 was prepared in analogy to example 1 strating from example 28a) and example 1b) to yield the title compound as a white solid (37(860 mg; 790%). m/z=601.1 [M+H]$^{+}$.

Example 30

(2S,4R)-4-(4-Bromo-2-chloro-benzenesulfonyl)-1-[1-(5-chloro-3-fluoro-pyridin-2-yl)-cyclopropanecarbonyl]-pyrrolidine-2-carboxylic acid (1-cyano-cyclopropyl)-amide

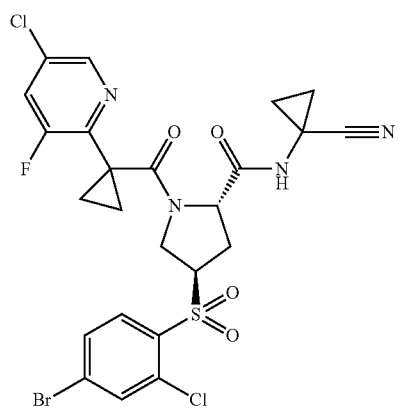 [SMILES: N#CC1(NC(=O)[C@@H]2C[C@@H](S(=O)(=O)c3ccc(Br)cc3Cl)CN2C(=O)C2(c3ncc(Cl)cc3F)CC2)CC1]

Example 30 was prepared in analogy to example 28 starting from 4-bromo-2-chlorobenzenethiol to yield the title compound as a white foam (860 mg; 79%) m/z=631.0 [M+H]$^{+}$.

Example 31

(2S,4R)-1-(1-(5-chloro-3-fluoropyridin-2-yl)cyclopropanecarbonyl)-4-(2-chloro-4-(2-methylpyridin-4-yl)phenylsulfonyl)-N-(1-cyanocyclopropyl)pyrrolidine-2-carboxamide

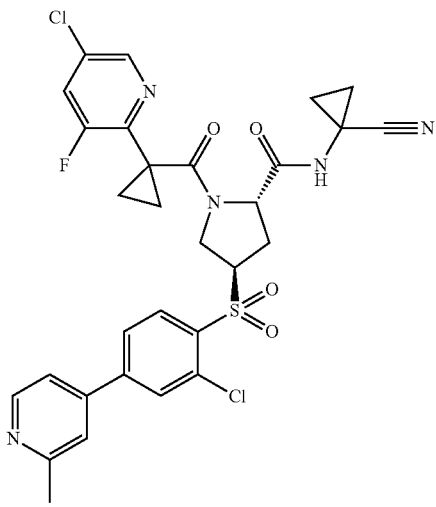 [SMILES: Cc1cc(-c2ccc(S(=O)(=O)[C@@H]3C[C@@H](C(=O)NC4(C#N)CC4)N(C(=O)C4(c5ncc(Cl)cc5F)CC4)C3)c(Cl)c2)ccn1]

Example 30 (100 mg, 159 μmol, Eq: 1.00) was dissolved in 1,2-dimethoxyethane (2 ml). 2-Methyl-4-(4,4,5,5-tetramethyl-1,3,2-dioxaborolan-2-yl)pyridine (45.2 mg, 206 μmol, Eq: 1.30), triphenylphosphine (8.32 mg, 31.7 μmol, Eq: 0.20), 2 M aqueous Na$_2$CO$_3$ solution (500 μl) and Pd(OAc)$_2$ (3.56 mg, 15.9 μmol, Eq: 0.10) were added and stirred at 45° C. for 4 h. The reaction mixture was poured into 0.1 M aqueous HCl solution (10 ml) and extracted with DCM (3×10 ml). The organic layers were dried over Na$_2$SO$_4$ and concentrated in vacuo. The crude material was purified by preparative HPLC to yield the title compound as an off-white foam (61 mg; 60%). m/z=642.1 [M+H]$^+$.

Example 32

(2S,4R)-4-[2-Chloro-4-(2-chloro-pyridin-4-yl)-benzenesulfonyl]-1-[1-(5-chloro-3-fluoro-pyridin-2-yl)-cyclopropanecarbonyl]-pyrrolidine-2-carboxylic acid (1-cyano-cyclopropyl)-amide

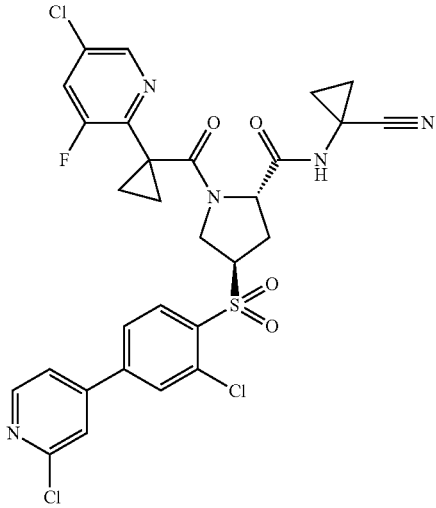 [SMILES: N#CC1(NC(=O)[C@@H]2C[C@@H](S(=O)(=O)c3ccc(-c4ccnc(Cl)c4)cc3Cl)CN2C(=O)C2(c3ncc(Cl)cc3F)CC2)CC1]

Example 32 was prepared in analogy to example 31 starting from example 30 and 2-chloro-4-(4,4,5,5-tetramethyl-1,3,2-dioxaborolan-2-yl)pyridine to yield the title compound as a white solid (27 mg; 26%) m/z=664.1 [M+H]$^+$.

Example 33

(2S,4R)-1-[1-(5-Chloro-3-fluoro-pyridin-2-yl)-cyclopropanecarbonyl]-4-[2-chloro-4-(1-methyl-1H-pyrazol-4-yl)-benzenesulfonyl]-pyrrolidine-2-carboxylic acid (1-cyano-cyclopropyl)-amide

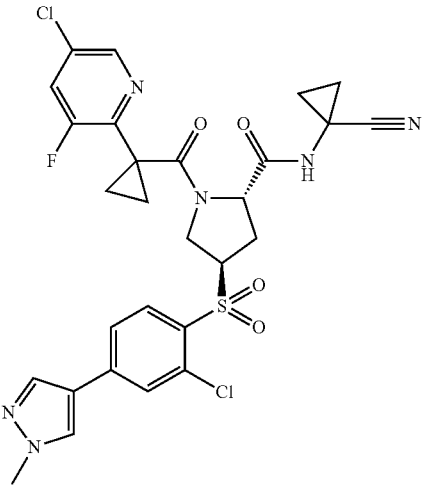 [SMILES: Cn1cc(-c2ccc(S(=O)(=O)[C@@H]3C[C@@H](C(=O)NC4(C#N)CC4)N(C(=O)C4(c5ncc(Cl)cc5F)CC4)C3)c(Cl)c2)cn1]

Example 33 was prepared in analogy to example 31 starting from example 30 and 1-methyl-4-(4,4,5,5-tetramethyl-1,3,2-dioxaborolan-2-yl)-1H-pyrazole to yield the title compound as a white solid (25 mg; 25%). m/z=631.1 [M+H]$^+$.

Example 34

(2S,4R)-1-[1-(5-Chloro-3-fluoro-pyridin-2-yl)-cyclopropanecarbonyl]-4-[2-chloro-4-(2-methyl-pyridin-3-yl)-benzenesulfonyl]-pyrrolidine-2-carboxylic acid (1-cyano-cyclopropyl)-amide

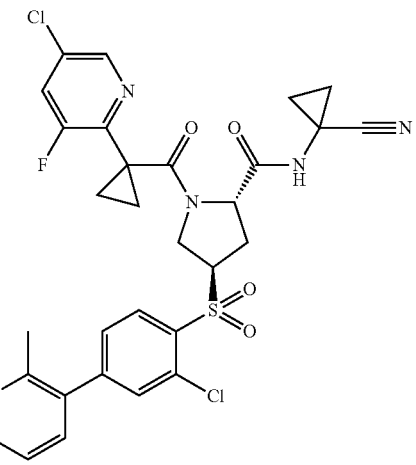

Example 34 was prepared in analogy to example 31 starting from example 30 and 2-methyl-3-(4,4,5,5-tetramethyl-1,3,2-dioxaborolan-2-yl)pyridine to yield the title compound as a white foam (47 mg; 38%) m/z=642.2 [M+H]$^+$.

Example 35

(2S,4R)-4-[2-Chloro-4-(2-methyl-pyridin-3-yl)-benzenesulfonyl]-1-[1-(3-fluoro-5-trifluoromethyl-pyridin-2-yl)-cyclopropanecarbonyl]-pyrrolidine-2-carboxylic acid (1-cyano-cyclopropyl)-amide

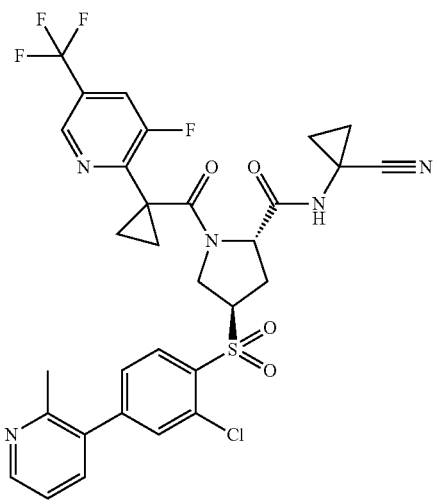 [SMILES: Cc1ncccc1-c1ccc(S(=O)(=O)[C@@H]2C[C@@H](C(=O)NC3(C#N)CC3)N(C(=O)C3(c4ncc(C(F)(F)F)cc4F)CC3)C2)c(Cl)c1]

a) (2S,4R)-4-(4-Bromo-2-chloro-benzenesulfonyl)-2-(1-cyano-cyclopropylcarbamoyl)-pyrrolidine-1-carboxylic acid tert-butyl ester

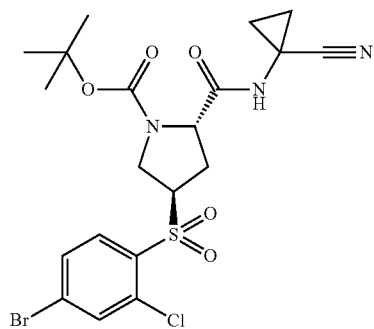 [SMILES: CC(C)(C)OC(=O)N1C[C@H](S(=O)(=O)c2ccc(Br)cc2Cl)C[C@H]1C(=O)NC1(C#N)CC1]

Example 35a) was prepared in analogy to the methods described for CAS 1252631-66-5 (see Haap et al.; US20100267722) starting from (2S,4R)-1,2-pyrrolidinedicarboxylic acid 4-hydroxy-1-(1,1-dimethylethyl) ester and 4-bromo-2-chloro-benzenethiol to yield the title compound as a white solid (3.2 g; 58%). m/z=434.1 [M+H-Boc]$^+$.

b) (2S,4R)-4-[2-Chloro-4-(2-methyl-pyridin-3-yl)-benzenesulfonyl]-2-(1-cyano-cyclopropylcarbamoyl)-pyrrolidine-1-carboxylic acid tert-butyl ester

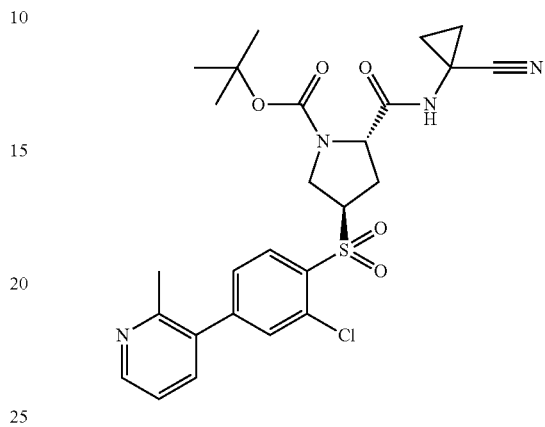

Example 35a) (700 mg, 1.31 mmol, Eq: 1.00) was dissolved in 1,2-dimethoxyethane (8 ml). 2-Methyl-3-(4,4,5,5-tetramethyl-1,3,2-dioxaborolan-2-yl)pyridine (345 mg, 1.58 mmol, Eq: 1.20), triphenylphosphine (68.9 mg, 263 µmol, Eq: 0.20), 2 M aqueous Na$_2$CO$_3$ solution (2 ml) and palladium (II) acetate (29.5 mg, 131 µmol, Eq: 0.10) were added and stirred at 22° C. for 24 h. After that, the reaction mixture was stirred at 50° C. for 24 h. Then, 2-methyl-3-(4,4,5,5-tetramethyl-1,3,2-dioxaborolan-2-yl)pyridine (57.6 mg, 263 µmol, Eq: 0.2) was added to the reaction mixture which was then stirred at 60° C. for 6 h. The reaction mixture was poured into 0.1 M aqueous HCl solution (50 ml) and extracted with DCM (3×20 ml). The organic layers were dried over Na$_2$SO$_4$ and concentrated in vacuo. The crude material was purified by flash chromatography (silica gel, 40 g, 0% to 100% EtOAc in heptane) to yield the title compound as a light yellow oil (200 mg; 28%). m/z=545.3 [M+H]$^+$.

c) (2S,4R)-4-[2-Chloro-4-(2-methyl-pyridin-3-yl)-benzenesulfonyl]-pyrrolidine-2-carboxylic acid (1-cyano-cyclopropyl)-amide

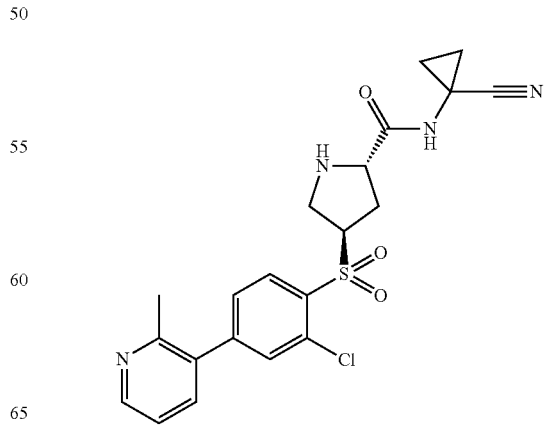

Example 35b) (200 mg, 367 μmol, Eq: 1.00) was dissolved in formic acid (2.4 g, 2 ml, 52.1 mmol, Eq: 142) and stirred at 22° C. for 15 h. The reaction mixture was adjusted carefully with icecold aqueous 10% Na$_2$CO$_3$-solution to pH 8 and extracted with CH$_2$Cl$_2$. The water layer was washed totally 3 times with CH$_2$Cl$_2$/THF (1:1; 30 ml), the combined organic layers were dried over Na$_2$SO$_4$, filtered and evaporated to yield the title compound as a white foam (142 mg; 87%). m/z=445.2 [M+H]$^+$.

d) 1-(3-Fluoro-5-trifluoromethyl-pyridin-2-yl)-cyclopropanecarboxylic acid

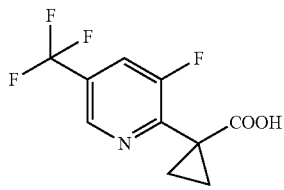 [SMILES: O=C(O)C1(c2ncc(C(F)(F)F)cc2F)CC1]

Example 35 d) was prepared in analogy to the methods described for examples 1a) and b) to yield the title compound as a light brown solid (50 mg; 41%) m/z=250.0 [M+H]$^+$.

e) (2S,4R)-4-[2-Chloro-4-(2-methyl-pyridin-3-yl)-benzenesulfonyl]-1-[1-(3-fluoro-5-trifluoromethyl-pyridin-2-yl)-cyclopropanecarbonyl]-pyrrolidine-2-carboxylic acid (1-cyano-cyclopropyl)-amide

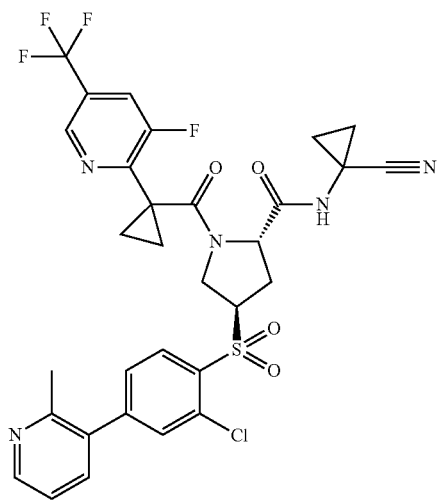 [SMILES: Cc1ncccc1-c1ccc(S(=O)(=O)[C@@H]2C[C@@H](C(=O)NC3(C#N)CC3)N(C(=O)C3(c4ncc(C(F)(F)F)cc4F)CC3)C2)c(Cl)c1]

The title compound was prepared in analogy to example 1d) starting from example 35c) (45 mg) and 35d) (30 mg) to yield an off-white solid (34 mg 50%) m/z=676.3 [M+H]$^+$.

Example 36

(2S,4R)-4-[2-Chloro-4-(2-methyl-pyridin-3-yl)-benzenesulfonyl]-1-[1-(3-fluoro-5-iodo-pyridin-2-yl)-cyclopropanecarbonyl]-pyrrolidine-2-carboxylic acid (1-cyano-cyclopropyl)-amide

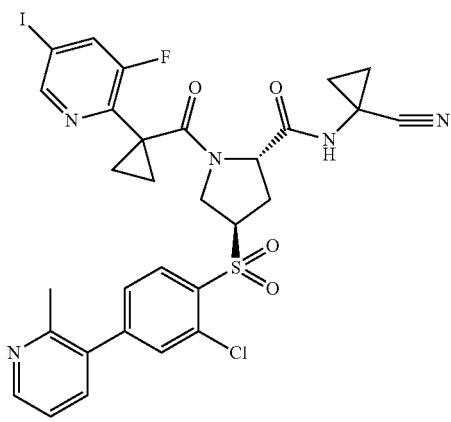 [SMILES: Cc1ncccc1-c1ccc(S(=O)(=O)[C@@H]2C[C@@H](C(=O)NC3(C#N)CC3)N(C(=O)C3(c4ncc(I)cc4F)CC3)C2)c(Cl)c1]

Example 36 was prepared in analogy to example 35 starting from example 35c) and 1-(3-fluoro-5-iodo-pyridin-2-yl)-cyclopropanecarboxylic acid, which was prepared in analogy to examples 1a) and 1b), to yield the title compound as a off-white solid (35 mg; 47%) m/z=734.2 [M+H]$^+$.

Example 37

(2S,4R)-4-[2-Chloro-4-(2-methyl-pyridin-3-yl)-benzenesulfonyl]-1-[1-(3,5-dichloro-pyridin-2-yl)-cyclopropanecarbonyl]-pyrrolidine-2-carboxylic acid (1-cyano-cyclopropyl)-amide

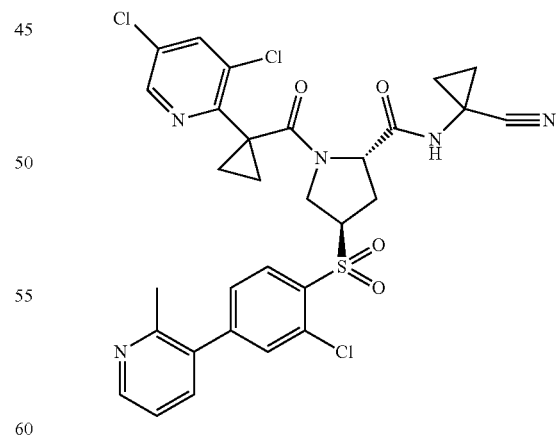

Example 37 was prepared in analogy to example 35 starting from example 35c) and 1-(5-chloro-3-fluoro-pyridin-2-yl)-cyclopropanecarboxylic acid, which was prepared in analogy to examples 1a) and 1b), to yield the title compound as an off-white solid (26 mg; 39%) m/z=660.2 [M+H]$^+$.

Example 38

(2S,4R)-4-[2-Chloro-4-(1-methyl-1H-pyrazol-4-yl)-
benzenesulfonyl]-1-[1-(3-fluoro-5-iodo-pyridin-2-
yl)-cyclopropanecarbonyl]-pyrrolidine-2-carboxylic
acid (1-cyano-cyclopropyl)-amide

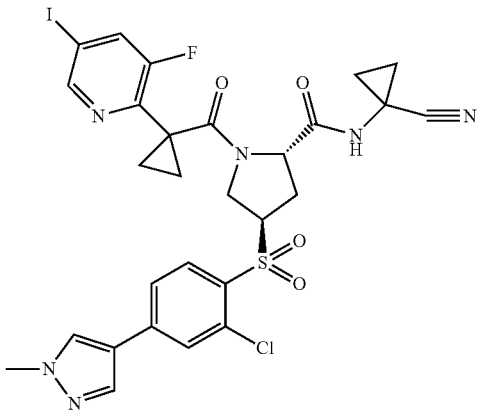 [SMILES: Cn1cc(-c2ccc(S(=O)(=O)[C@@H]3C[C@@H](C(=O)NC4(C#N)CC4)N(C(=O)C4(c5ncc(I)cc5F)CC4)C3)c(Cl)c2)cn1]

a) (2S,4R)-4-[2-Chloro-4-(1-methyl-1H-pyrazol-4-
yl)-benzenesulfonyl]-pyrrolidine-2-carboxylic acid
(1-cyano-cyclopropyl)-amide

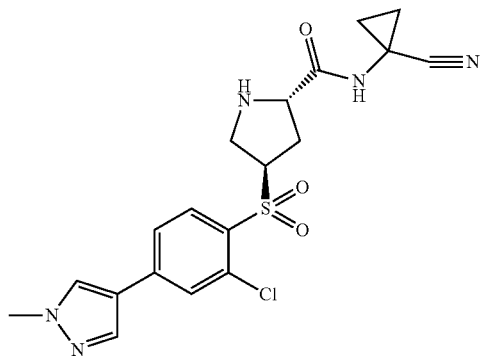 [SMILES: Cn1cc(-c2ccc(S(=O)(=O)[C@H]3CN[C@H](C(=O)NC4(C#N)CC4)C3)c(Cl)c2)cn1]

Example 38a) was prepared in analogy to example 35c) starting from examples 35a) and 1-methyl-4-(4,4,5,5-tetramethyl-1,3,2-dioxaborolan-2-yl)-1H-pyrazole to yield the title compound as a light brown foam (173 mg; 95%). m/z=434.2 [M+H]⁺.

b) (2S,4R)-4-[2-Chloro-4-(1-methyl-1H-pyrazol-4-
yl)-benzenesulfonyl]-1-[1-(3-fluoro-5-iodo-pyridin-
2-yl)-cyclopropanecarbonyl]-pyrrolidine-2-carboxy-
lic acid (1-cyano-cyclopropyl)-amide

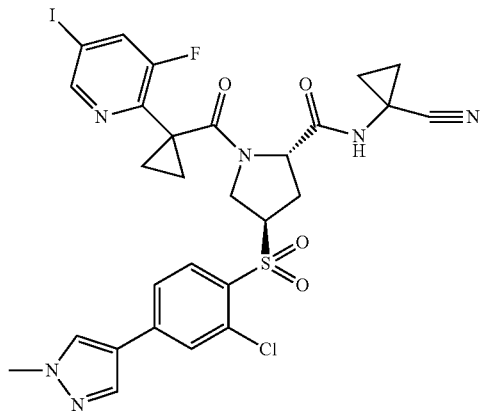 [SMILES: Cn1cc(-c2ccc(S(=O)(=O)[C@@H]3C[C@@H](C(=O)NC4(C#N)CC4)N(C(=O)C4(c5ncc(I)cc5F)CC4)C3)c(Cl)c2)cn1]

Example 38b) was prepared in analogy to example 35 starting from example 38a) and 1-(3-fluoro-5-iodo-pyridin-2-yl)-cyclopropanecarboxylic acid, which was prepared in analogy to examples 1a) and 1b), to yield the title compound as a off-white solid (40 mg; 48%) m/z=723.1 [M+H]⁺.

Example 39

(2S,4R)-4-[2-Chloro-4-(1-methyl-1H-pyrazol-4-yl)-
benzenesulfonyl]-1-[1-(3-fluoro-5-trifluoromethyl-
pyridin-2-yl)-cyclopropanecarbonyl]-pyrrolidine-2-
carboxylic acid (1-cyano-cyclopropyl)-amide

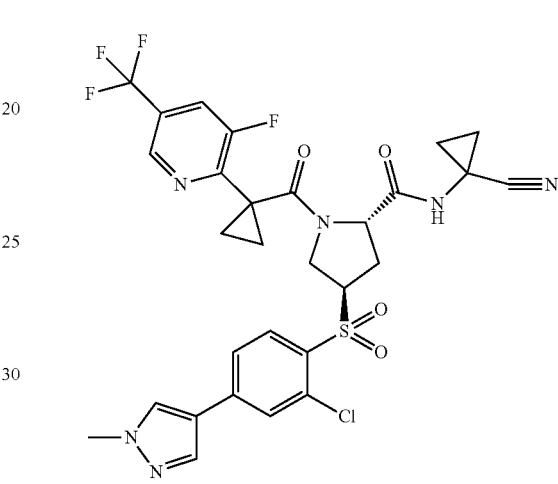

Example 39 was prepared in analogy to example 38b) starting from example 38a) and 35d) to yield the title compound as a off-white solid (16 mg; 60%). m/z=665.1 [M+H]⁺.

Example 40

(2S,4R)-4-[2-Chloro-4-(1-methyl-1H-pyrazol-4-yl)-
benzenesulfonyl]-1-[1-(3,5-dichloro-pyridin-2-yl)-
cyclopropanecarbonyl]-pyrrolidine-2-carboxylic acid
(1-cyano-cyclopropyl)-amide

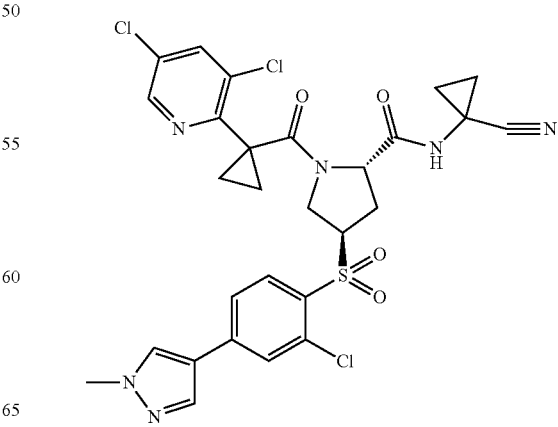

Example 40 was prepared in analogy to example 35 starting from example 38a) and 1-(3,5-dichloro-pyridin-2-yl)-cyclopropanecarboxylic acid, which was prepared in analogy to examples 1a) and 1b), to yield the title compound as an off-white solid (29 mg; 39%) m/z=649.2 [M+H]⁺.

Example 41

(2S,4R)-4-(2-Fluoro-benzenesulfonyl)-1-[1-(3-fluoro-5-iodo-pyridin-2-yl)-cyclopropanecarbonyl]-pyrrolidine-2-carboxylic acid (1-cyano-cyclopropyl)-amide

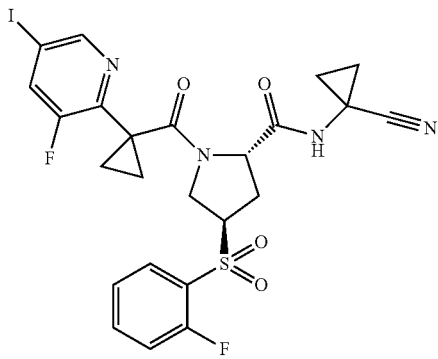 [SMILES: N#CC1(NC(=O)[C@@H]2C[C@@H](S(=O)(=O)c3ccccc3F)CN2C(=O)C2(c3ncc(I)cc3F)CC2)CC1]

Example 41 was prepared in analogy to example 8 starting from 2-fluorobenzenethiol and 1-(3-fluoro-5-iodo-pyridin-2-yl)-cyclopropanecarboxylic acid to yield the title compound as a white foam (328 mg; 68%). m/z=627.3 [M+H]⁺.

Example 42

(2S,4R)-1-[1-(5-Chloro-3-fluoro-pyridin-2-yl)-cyclopropanecarbonyl]-4-(2-fluoro-benzenesulfonyl)-pyrrolidine-2-carboxylic acid (1-cyano-cyclopropyl)-amide

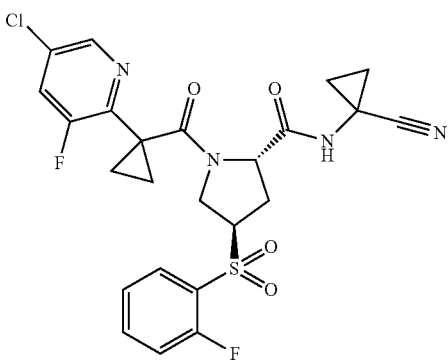 [SMILES: N#CC1(NC(=O)[C@@H]2C[C@@H](S(=O)(=O)c3ccccc3F)CN2C(=O)C2(c3ncc(Cl)cc3F)CC2)CC1]

Example 42 was prepared in analogy to example 41 starting from 2-fluorobenzenethiol and 1-(5-chloro-3-fluoro-pyridin-2-yl)-cyclopropanecarboxylic acid to yield the title compound as a white foam (212 mg; 67%). m/z=535.4 [M+H]⁺.

Example 43

(2S,4R)-1-[1-(3-Fluoro-5-iodo-pyridin-2-yl)-cyclopropanecarbonyl]-4-(2-pyrazol-1-yl-benzenesulfonyl)-pyrrolidine-2-carboxylic acid (1-cyano-cyclopropyl)-amide

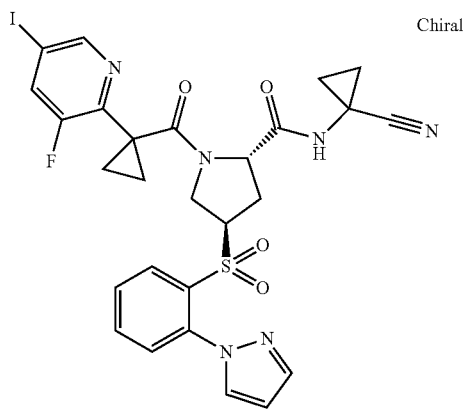 [SMILES: N#CC1(NC(=O)[C@@H]2C[C@@H](S(=O)(=O)c3ccccc3-n3cccn3)CN2C(=O)C2(c3ncc(I)cc3F)CC2)CC1]

To a 5 mL tube were added example 41 (60 mg, 95.8 µmol, Eq: 1.00), 1H-pyrazole (9.78 mg, 144 µmol, Eq: 1.50), Cs₂CO₃ (37.4 mg, 115 µmol, Eq: 1.20) and DMF (1 ml). The reaction mixture was stirred for 24 h at 22° C. To the reaction mixture was again 1H-pyrazole (9.78 mg, 144 µmol, Eq: 1.50) added and stirred for 24 h at 50° C. The crude material was purified by preparative HPLC to yield the title compound as a white foam (8 mg; 12.4%). m/z=675.0647 [M+H]⁺.

Example 44

(2S,4R)-1-[1-(3-Fluoro-5-iodo-pyridin-2-yl)-cyclopropanecarbonyl]-4-(2-[1,2,3]triazol-1-yl-benzenesulfonyl)-pyrrolidine-2-carboxylic acid (1-cyano-cyclopropyl)-amide

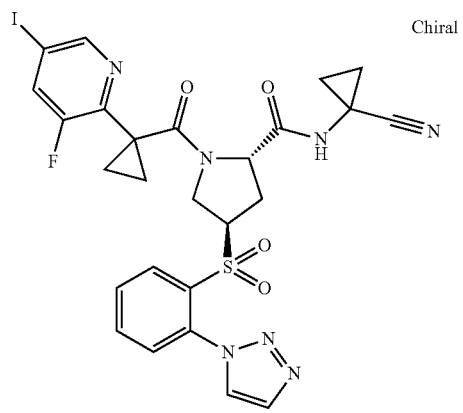 [SMILES: N#CC1(NC(=O)[C@@H]2C[C@@H](S(=O)(=O)c3ccccc3-n3ccnn3)CN2C(=O)C2(c3ncc(I)cc3F)CC2)CC1]

To a 5 mL tube were added example 41 (60 mg, 95.8 µmol, Eq: 1.00), 1H-1,2,3-triazole (9.92 mg, 8.32 µl, 144 µmol, Eq: 1.50), Cs₂CO₃ (37.4 mg, 115 µmol, Eq: 1.20) and DMA (1 ml). The reaction mixture was stirred for 24 h at 22° C. To the reaction mixture was again 1H-1,2,3-triazole (9.92 mg, 8.32 µl, 144 µmol, Eq: 1.50) added and stirred for 24 h at 50° C. The crude material was purified by preparative HPLC to yield the title compound as a white foam (25 mg; 23%; purity 50-80%). m/z=676.0638 [M+H]⁺.

Example 45

(2S,4R)-1-[1-(3-Fluoro-5-iodo-pyridin-2-yl)-cyclopropanecarbonyl]-4-(2-[1,2,4]triazol-1-yl-benzenesulfonyl)-pyrrolidine-2-carboxylic acid (1-cyanocyclopropyl)-amide

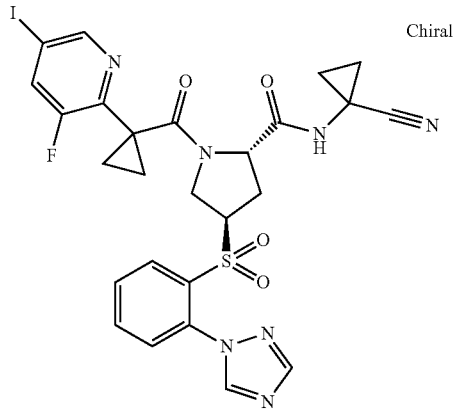 [SMILES: N#CC1(NC(=O)[C@@H]2C[C@@H](S(=O)(=O)c3ccccc3-n3cncn3)CN2C(=O)C2(c3ncc(I)cc3F)CC2)CC1]

To a 5 mL tube were added example 41 (60 mg, 95.8 µmol, Eq: 1.00), 1H-1,2,4-triazole (9.92 mg, 144 µmol, Eq: 1.50), 1H-1,2,4-triazole (9.92 mg, 144 µmol, Eq: 1.50) and DMA (1 ml). The reaction mixture was stirred for 24 h at 22° C. To the reaction mixture was again 1H-1,2,4-triazole (9.92 mg, 144 µmol, Eq: 1.50) added and stirred for 24 h at 50° C. The crude material was purified by preparative HPLC to the title compound as a white foam (15 mg; 18.8%; purity 50-80%). m/z=676.0629 [M+H]⁺.

Example 46

((2S,4R)-1-[1-(5-Chloro-3-fluoro-pyridin-2-yl)-cyclopropanecarbonyl]-4-(2-pyrazol-1-yl-benzenesulfonyl)-pyrrolidine-2-carboxylic acid (1-cyanocyclopropyl)-amide

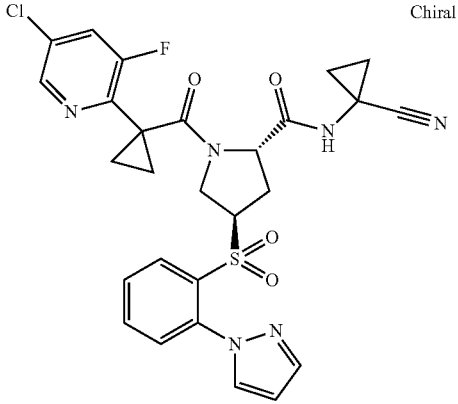 [SMILES: N#CC1(NC(=O)[C@@H]2C[C@@H](S(=O)(=O)c3ccccc3-n3cccn3)CN2C(=O)C2(c3ncc(Cl)cc3F)CC2)CC1]

To a 5 mL tube were added example 42 (50 mg, 93.5 µmol, Eq: 1.00), 1H-pyrazole (9.54 mg, 140 µmol, Eq: 1.50), Cs₂CO₃ (36.5 mg, 112 µmol, Eq: 1.20) and DMA (1 ml). The reaction mixture was stirred for 24 h at 22° C. To the reaction mixture was again 1H-pyrazole (9.54 mg, 140 µmol, Eq: 1.50) added and stirred for 24 h at 50° C. The crude material was purified by preparative HPLC to yield the title compound as a white foam (10 mg; 15%; purity 80%). m/z=583.1319 [M+H]⁺.

Example 47

(2S,4R)-1-[1-(5-Chloro-3-fluoro-pyridin-2-yl)-cyclopropanecarbonyl]-4-(2-[1,2,3]triazol-1-yl-benzenesulfonyl)-pyrrolidine-2-carboxylic acid (1-cyanocyclopropyl)-amide

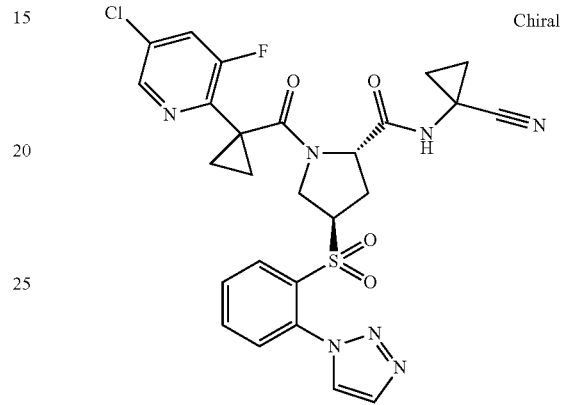

To a 5 mL tube were added example 42 (50 mg, 93.5 µmol, Eq: 1.00), 1H-1,2,3-triazole (9.68 mg, 8.12 µl, 140 µmol, Eq: 1.50), Cs2CO3 (36.5 mg, 112 µmol, Eq: 1.20) and DMA (1 ml). The reaction mixture was stirred for 24 h at 22° C. To the reaction mixture was again 1H-1,2,3-triazole (9.68 mg, 8.12 µl, 140 µmol, Eq: 1.50) added and stirred for 24 h at 50° C. The crude material was purified by preparative HPLC to yield the title compound as a white foam (10 mg; 11%; purity 60%). m/z=584.1272 [M+H]⁺.

Example 48

(2S,4R)-1-[1-(5-Chloro-3-fluoro-pyridin-2-yl)-cyclopropanecarbonyl]-4-(2-[1,2,4]triazol-1-yl-benzenesulfonyl)-pyrrolidine-2-carboxylic acid (1-cyanocyclopropyl)-amide

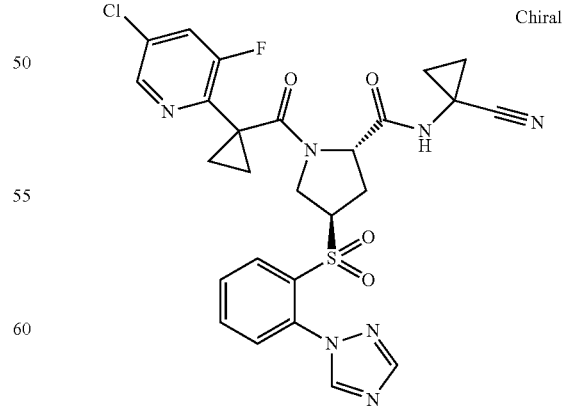

To a 5 mL tube were added example 42 (50 mg, 93.5 µmol, Eq: 1.00), 1H-1,2,4-triazole (9.68 mg, 140 µmol, Eq: 1.50), Cs₂CO₃ (36.5 mg, 112 µmol, Eq: 1.20) and DMA (1 ml). The reaction mixture was stirred for 24 h at 22° C. To the reaction mixture was again 1H-1,2,4-triazole (9.68 mg, 140 µmol, Eq: 1.50) added and stirred for 24 h at 50° C. The crude material was purified by preparative HPLC to yield the title compound as a white foam (25 mg; 35%; purity 77%). m/z=584.1281 [M+H]$^+$.

Example 49

Cathepsin Enzyme Inhibition Assay

Enzyme activity is measured by observing the increase in fluorescence intensity caused by cleavage of a peptide substrate containing a fluorophore whose emission is quenched in the intact peptide.

Assay buffer: 100 mM potassium phosphate pH 6.5, EDTA-Na 5 mM, Triton X-100 0.001%, DTT 5 mM.

Enzymes (all at 1 nM): human and mouse Cathepsin S, Cat K, Cat B, Cat L.

Substrate (20 µM): Z-Val-Val-Arg-AMC, except for Cat K which uses Z-Leu-Arg-AMC (both from Bachem).

Z=Benzyloxycarbonyl.
AMC=7-Amino-4-Methyl-Coumarin.
DTT=dithiothreitol.
Final volume: 100 µL.
Excitation 360 nm, Emission 465 nm.

Enzyme is added to the substance dilutions in 96-well microtitre plates and the reaction is started with substrate. Fluorescence emission is measured over 20 minutes, during which time a linear increase is observed in the absence of inhibitor. IC$_{50}$ are calculated by standard methods.

Inhibition of human Cat S, mouse Cat S, human Cat K, human Cat B, human Cat L and mouse Cat L have been measured separately. The results obtained for human Cat S and L for representative compounds of the invention are expressed in the following table in µM.

| Example | IC50 h S | IC50 h L |
| --- | --- | --- |
| 1 | 0.000606 | 0.4097 |
| 2 | 0.000492 | 0.3402 |
| 3 | 0.000825 | 0.429 |
| 4 | 0.000393 | 0.0119 |
| 5 | 0.000398 | 0.0129 |
| 6 | 0.000675 | 0.0445 |
| 7 | 0.000734 | 0.0255 |
| 8 | 0.000438 | 0.0192 |
| 9 | 0.011785 | 0.4165 |
| 10 | 0.96365 | 15.8722 |
| 11 | 0.000602 | 0.0898 |
| 12 | 0.5941 | 8.2265 |
| 13 | 0.00077 | 0.2474 |
| 14 | 0.002844 | 2.117 |
| 15 | 0.011075 | 1.679 |
| 16 | 1.031 | >25 |
| 17 | 0.2635 | 5.648 |
| 18 | 0.00424 | 3.4345 |
| 19 | 0.12715 | 4.6095 |
| 20 | 0.3926 | 5.0635 |
| 21 | 0.27455 | 10.011 |
| 22 | 0.002996 | 1.9695 |
| 23 | 0.002796 | 5.635 |
| 24 | 0.006244 | 2.694 |
| 25 | 0.003213 | 13.1975 |
| 26 | 0.003466 | 0.0524 |
| 27 | 0.001596 | 0.09 |
| 28 | 0.000543 | 0.0568 |
| 29 | 0.000618 | 0.3618 |
| 30 | 0.000474 | 0.0726 |
| 31 | 0.000505 | 0.0616 |
| 32 | 0.000686 | 0.1121 |
| 33 | 0.000375 | 0.0287 |
| 34 | 0.000322 | 0.0642 |
| 35 | 0.000768 | 0.0589 |
| 36 | 0.000382 | 0.0098 |
| 37 | 0.000779 | 0.0722 |
| 38 | 0.000678 | 0.0032 |
| 39 | 0.000696 | 0.0436 |
| 40 | 0.000703 | 0.1111 |
| 41 | 0.0006 | 0.003 |
| 42 | 0.0007 | 0.031 |
| 43 | 0.016985 | 0.0906 |
| 44 | 0.002372 | 1.5585 |
| 45 | 0.3272 | 28.383 |
| 46 | 0.1587 | 17.445 |
| 47 | 0.004268 | 35.2 |
| 48 | 0.058535 | 21.1025 |

The compounds of the invention are preferential inhibitors of Cathepsin-S and L over Cathepsin-K and B.

The compounds according to the invention have, in the foregoing assay, an IC$_{50}$ at Cat S and/or L which is between 0.00001 and 100 µM. Particular compounds of the invention have an IC50 at Cat S and/or L between 0.00001 and 50 µM and mor particularly between 0.00001 and 20 µM. The particular compounds of the invention have an IC$_{50}$ in at least one of the foregoing assay below 0.09 µM.

Example A

A compound of formula (I) can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:
1. A compound of formula (I)

wherein
$A^1$ is —S— or —S(O)$_2$—;
$A^2$ is nitrogen or —(CH)—;
$R^1$ is halogen or haloalkyl;
$R^2$ is hydrogen or halogen;
$R^3$ is hydrogen, halogen, haloalkyl, pyrazolyl, [1,2,3]-triazolyl or [1,2,4]-triazolyl;
$R^4$ and $R^6$ are independently selected from hydrogen, alkyl, haloalkyl and halophenyl; and
$R^5$ is hydrogen, halogen, haloalkyl, alkoxy, haloalkoxy, alkylpyridinyl, halopyridinyl or alkylpyrazolyl;
or a pharmaceutically acceptable salt thereof.
2. The compound of claim 1, wherein $A^1$ is —S(O)$_2$—.
3. The compound of claim 1, wherein $A^2$ is —(CH)—.
4. The compound of claim 1, wherein $R^1$ is chloro, bromo, iodo or trifluoromethyl.
5. The compound of claim 1, wherein $R^2$ is halogen.
6. The compound of claim 1, wherein $R^2$ is chloro or fluoro.
7. The compound of claim 1, wherein $R^3$ is halogen.
8. The compound of claim 1, wherein $R^3$ is chloro.
9. The compound of claim 1, wherein $R^4$ and $R^6$ are independently selected from hydrogen and haloalkyl.
10. The compound of claim 1, wherein $R^4$ and $R^6$ are independently selected from hydrogen and trifluoromethyl.
11. The compound of claim 1, wherein $R^5$ is hydrogen, alkoxy, haloalkoxy, halogen, alkylpyridinyl or alkylpyrazolyl.
12. The compound of claim 1, wherein $R^5$ is hydrogen, methoxy, trifluoroethoxy, fluoro, trifluoropropyloxy, bromo, methylpyridinyl or methylpyrazolyl.
13. A compound selected from
(2S,4R)-4-(2-Chloro-4-methoxy-benzenesulfonyl)-1-[1-(5-chloro-pyridin-2-yl)-cyclopropanecarbonyl]-pyrrolidine-2-carboxylic acid (1-cyano-cyclopropyl)-amide;
(2S,4R)-4-(2-Chloro-benzenesulfonyl)-1-[1-(5-chloro-pyridin-2-yl)-cyclopropanecarbonyl]-pyrrolidine-2-carboxylic acid (1-cyano-cyclopropyl)-amide;
(2S,4R)-1-[1-(5-Chloro-pyridin-2-yl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide;
(2S,4R)-1-[1-(5-Chloro-3-fluoro-pyridin-2-yl)-cyclopropanecarbonyl]-4-(2-chloro-4-methoxy-benzenesulfonyl)-pyrrolidine-2-carboxylic acid (1-cyano-cyclopropyl)-amide;
(2S,4R)-4-(2-Chloro-benzenesulfonyl)-1-[1-(5-chloro-3-fluoro-pyridin-2-yl)-cyclopropanecarbonyl]-pyrrolidine-2-carboxylic acid (1-cyano-cyclopropyl)-amide;
(2S,4R)-1-[1-(5-Chloro-3-fluoro-pyridin-2-yl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide;
(2S,4R)-1-[1-(5-Bromo-3-fluoro-pyridin-2-yl)-cyclopropanecarbonyl]-4-(2-chloro-4-methoxy-benzenesulfonyl)-pyrrolidine-2-carboxylic acid (1-cyano-cyclopropyl)-amide;
(2S,4R)-1-[1-(5-Bromo-3-fluoro-pyridin-2-yl)-cyclopropanecarbonyl]-4-(2-chloro-benzenesulfonyl)-pyrrolidine-2-carboxylic acid (1-cyano-cyclopropyl)-amide;
(2S,4R)-1-[1-(5-Chloro-3-fluoro-pyridin-2-yl)-cyclopropanecarbonyl]-4-(4'-fluoro-biphenyl-3-ylsulfanyl)-pyrrolidine-2-carboxylic acid (1-cyano-cyclopropyl)-amide;
(2S,4R)-1-[1-(5-Chloro-3-fluoro-pyridin-2-yl)-cyclopropanecarbonyl]-4-(3-chloro-pyridin-2-ylsulfanyl)-pyrrolidine-2-carboxylic acid (1-cyano-cyclopropyl)-amide;
(2S,4R)-1-(1-(5-chloro-3-fluoropyridin-2-yl)cyclopropanecarbonyl)-4-(2-chloro-4-fluorophenylsulfonyl)-N-(1-cyanocyclopropyl)pyrrolidine-2-carboxamide;
(2S,4R)-1-[1-(5-Chloro-3-fluoro-pyridin-2-yl)-cyclopropanecarbonyl]-4-(pyridin-2-ylsulfanyl)-pyrrolidine-2-carboxylic acid (1-cyano-cyclopropyl)-amide;
(2S,4R)-1-[1-(5-Chloro-3-fluoro-pyridin-2-yl)-cyclopropanecarbonyl]-4-(4'-fluoro-biphenyl-3-sulfonyl)-pyrrolidine-2-carboxylic acid (1-cyano-cyclopropyl)-amide;
(2S,4R)-1-[1-(5-Chloro-3-fluoro-pyridin-2-yl)-cyclopropanecarbonyl]-4-(3-chloro-pyridine-2-sulfonyl)-pyrrolidine-2-carboxylic acid (1-cyano-cyclopropyl)-amide;
(2S,4S)-4-(2-Chloro-4-fluoro-benzenesulfonyl)-1-[1-(5-chloro-3-fluoro-pyridin-2-yl)-cyclopropanecarbonyl]-pyrrolidine-2-carboxylic acid (1-cyano-cyclopropyl)-amide;
(2S,4R)-1-[1-(5-Chloro-3-fluoro-pyridin-2-yl)-cyclopropanecarbonyl]-4-(3-chloro-5-trifluoromethyl-pyridin-2-ylsulfanyl)-pyrrolidine-2-carboxylic acid (1-cyano-cyclopropyl)-amide;
(2S,4R)-1-[1-(5-Chloro-3-fluoro-pyridin-2-yl)-cyclopropanecarbonyl]-4-(5-chloro-pyridin-2-ylsulfanyl)-pyrrolidine-2-carboxylic acid (1-cyano-cyclopropyl)-amide;
(2S,4R)-1-[1-(5-Chloro-3-fluoro-pyridin-2-yl)-cyclopropanecarbonyl]-4-(pyridine-2-sulfonyl)-pyrrolidine-2-carboxylic acid (1-cyano-cyclopropyl)-amide;
(2S,4R)-1-[1-(5-Chloro-3-fluoro-pyridin-2-yl)-cyclopropanecarbonyl]-4-(6-methyl-pyridin-2-ylsulfanyl)-pyrrolidine-2-carboxylic acid (1-cyano-cyclopropyl)-amide;
(2S,4R)-1-[1-(5-Chloro-3-fluoro-pyridin-2-yl)-cyclopropanecarbonyl]-4-(5-trifluoromethyl-pyridin-2-ylsulfanyl)-pyrrolidine-2-carboxylic acid (1-cyano-cyclopropyl)-amide;
(2S,4R)-1-[1-(5-Chloro-3-fluoro-pyridin-2-yl)-cyclopropanecarbonyl]-4-(3-trifluoromethyl-pyridin-2-ylsulfanyl)-pyrrolidine-2-carboxylic acid (1-cyano-cyclopropyl)-amide;
(2S,4R)-1-[1-(5-Chloro-3-fluoro-pyridin-2-yl)-cyclopropanecarbonyl]-4-(5-chloro-pyridine-2-sulfonyl)-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(6-methyl-pyridine-2-sulfonyl)-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(5-trifluoromethyl-pyridine-2-sulfonyl)-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(3-trifluoromethyl-pyridine-2-sulfonyl)-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(2-chloro-5-trifluoromethyl-phenylsulfanyl)-pyrrolidine-2-carboxylic acid (1-cyano-cyclopropyl)-amide;

(2S,4R)-1-(1-(5-chloro-3-fluoropyridin-2-yl)cyclopropanecarbonyl)-4-(2-chloro-4-((S)-1,1,1-trifluoropropan-2-yloxy)phenylsulfonyl)-N-(1-cyanocyclopropyl) pyrrolidine-2-carboxamide;

(2S,4R)-1-(1-(5-chloro-3-fluoropyridin-2-yl)cyclopropanecarbonyl)-4-(2-chloro-5-(trifluoromethyl)phenylsulfonyl)-N-(1-cyanocyclopropyl)pyrrolidine-2-carboxamide;

(2S,4R)-1-[1-(5-Chloro-pyridin-2-yl)-cyclopropanecarbonyl]-4-(2-chloro-5-trifluoromethyl-benzenesulfonyl)-pyrrolidine-2-carboxylic acid (1-cyano-cyclopropyl)-amide;

(2S,4R)-4-(4-Bromo-2-chloro-benzenesulfonyl)-1-[1-(5-chloro-3-fluoro-pyridin-2-yl)-cyclopropanecarbonyl]-pyrrolidine-2-carboxylic acid (1-cyano-cyclopropyl)-amide;

(2S,4R)-1-(1-(5-chloro-3-fluoropyridin-2-yl)cyclopropanecarbonyl)-4-(2-chloro-4-(2-methylpyridin-4-yl) phenylsulfonyl)-N-(1-cyanocyclopropyl)pyrrolidine-2-carboxamide;

(2S,4R)-4-[2-Chloro-4-(2-chloro-pyridin-4-yl)-benzenesulfonyl]-1-[1-(5-chloro-3-fluoro-pyridin-2-yl)-cyclopropanecarbonyl]-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-[2-chloro-4-(1-methyl-1H-pyrazol-4-yl)-benzenesulfonyl]-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-[2-chloro-4-(2-methyl-pyridin-3-yl)-benzenesulfonyl]-pyrrolidine-2-carboxylic acid (1-cyano-cyclopropyl)-amide;

(2S,4R)-4-[2-Chloro-4-(2-methyl-pyridin-3-yl)-benzenesulfonyl]-1-[1-(3-fluoro-5-trifluoromethyl-pyridin-2-yl)-cyclopropanecarbonyl]-pyrrolidine-2-carboxylic acid (1-cyano-cyclopropyl)-amide;

(2S,4R)-4-[2-Chloro-4-(2-methyl-pyridin-3-yl)-benzenesulfonyl]-1-[1-(3-fluoro-5-iodo-pyridin-2-yl)-cyclopropanecarbonyl]-pyrrolidine-2-carboxylic acid (1-cyano-cyclopropyl)-amide;

(2S,4R)-4-[2-Chloro-4-(2-methyl-pyridin-3-yl)-benzenesulfonyl]-1-[1-(3,5-dichloro-pyridin-2-yl)-cyclopropanecarbonyl]-pyrrolidine-2-carboxylic acid (1-cyano-cyclopropyl)-amide;

(2S,4R)-4-[2-Chloro-4-(1-methyl-1H-pyrazol-4-yl)-benzenesulfonyl]-1-[1-(3-fluoro-5-iodo-pyridin-2-yl)-cyclopropanecarbonyl]-pyrrolidine-2-carboxylic acid (1-cyano-cyclopropyl)-amide;

(2S,4R)-4-[2-Chloro-4-(1-methyl-1H-pyrazol-4-yl)-benzenesulfonyl]-1-[1-(3-fluoro-5-trifluoromethyl-pyridin-2-yl)-cyclopropanecarbonyl]-pyrrolidine-2-carboxylic acid (1-cyano-cyclopropyl)-amide;

(2S,4R)-4-[2-Chloro-4-(1-methyl-1H-pyrazol-4-yl)-benzenesulfonyl]-1-[1-(3,5-dichloro-pyridin-2-yl)-cyclopropanecarbonyl]-pyrrolidine-2-carboxylic acid (1-cyano-cyclopropyl)-amide;

(2S,4R)-4-(2-Fluoro-benzenesulfonyl)-1-[1-(3-fluoro-5-iodo-pyridin-2-yl)-cyclopropanecarbonyl]-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(2-fluoro-benzenesulfonyl)-pyrrolidine-2-carboxylic acid (1-cyano-cyclopropyl)-amide;

(2S,4R)-1-[1-(3-Fluoro-5-iodo-pyridin-2-yl)-cyclopropanecarbonyl]-4-(2-pyrazol-1-yl-benzenesulfonyl)-pyrrolidine-2-carboxylic acid (1-cyano-cyclopropyl)-amide;

(2S,4R)-1-[1-(3-Fluoro-5-iodo-pyridin-2-yl)-cyclopropanecarbonyl]-4-(2-[1,2,3]triazol-1-yl-benzenesulfonyl)-pyrrolidine-2-carboxylic acid (1-cyano-cyclopropyl)-amide;

(2S,4R)-1-[1-(3-Fluoro-5-iodo-pyridin-2-yl)-cyclopropanecarbonyl]-4-(2-[1,2,4]triazol-1-yl-benzenesulfonyl)-pyrrolidine-2-carboxylic acid (1-cyano-cyclopropyl)-amide;

((2S,4R)-1-[1-(5-Chloro-3-fluoro-pyridin-2-yl)-cyclopropanecarbonyl]-4-(2-pyrazol-1-yl-benzenesulfonyl)-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-(2-[1,2,3]triazol-1-yl-benzenesulfonyl)-pyrrolidine-2-carboxylic acid (1-cyano-cyclopropyl)-amide; or (2S,4R)-1-[1-(5-Chloro-3-fluoro-pyridin-2-yl)-cyclopropanecarbonyl]-4-(2-[1,2,4]triazol-1-yl-benzenesulfonyl)-pyrrolidine-2-carboxylic acid (1-cyano-cyclopropyl)-amide, or a pharmaceutically acceptable salt thereof.

14. A compound selected from (2S,4R)-1-[1-(5-Chloro-3-fluoro-pyridin-2-yl)-cyclopropanecarbonyl]-4-(2-chloro-4-methoxy-benzenesulfonyl)-pyrrolidine-2-carboxylic acid (1-cyano-cyclopropyl)-amide;

(2S,4R)-4-(2-Chloro-benzenesulfonyl)-1-[1-(5-chloro-3-fluoro-pyridin-2-yl)-cyclopropanecarbonyl]-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-1-[1-(5-Bromo-3-fluoro-pyridin-2-yl)-cyclopropanecarbonyl]-4-(2-chloro-4-methoxy-benzenesulfonyl)-pyrrolidine-2-carboxylic acid (1-cyano-cyclopropyl)-amide;

(2S,4R)-1-[1-(5-Bromo-3-fluoro-pyridin-2-yl)-cyclopropanecarbonyl]-4-(2-chloro-benzenesulfonyl)-pyrrolidine-2-carboxylic acid (1-cyano-cyclopropyl)-amide;

(2S,4R)-1-(1-(5-chloro-3-fluoropyridin-2-yl)cyclopropanecarbonyl)-4-(2-chloro-4-fluorophenylsulfonyl)-N-(1-cyanocyclopropyl)pyrrolidine-2-carboxamide;

(2S,4R)-1-(1-(5-chloro-3-fluoropyridin-2-yl)cyclopropanecarbonyl)-4-(2-chloro-4-((S)-1,1,1-trifluoropropan-2-yloxy)phenylsulfonyl)-N-(1-cyanocyclopropyl) pyrrolidine-2-carboxamide;

(2S,4R)-1-(1-(5-chloro-3-fluoropyridin-2-yl)cyclopropanecarbonyl)-4-(2-chloro-5-(trifluoromethyl)phenylsulfonyl)-N-(1-cyanocyclopropyl)pyrrolidine-2-carboxamide;

(2S,4R)-4-(4-Bromo-2-chloro-benzenesulfonyl)-1-[1-(5-chloro-3-fluoro-pyridin-2-yl)-cyclopropanecarbonyl]-pyrrolidine-2-carboxylic acid (1-cyano-cyclopropyl)-amide;

(2S,4R)-1-(1-(5-chloro-3-fluoropyridin-2-yl)cyclopropanecarbonyl)-4-(2-chlor-4-(2-methylpyridin-4-yl)phenylsulfonyl)-N-(1-cyanocyclopropyl)pyrrolidine-2-carboxamide;

(2S,4R)-1-[1-(5-Chloro-3-fluoro-pyridin-2-yl)-cyclopropanecarbonyl]-4-[2-chloro-4-(1-methyl-1H-pyrazol-4-yl)-benzenesulfonyl]-pyrrolidine-2-carboxylic acid (1-cyano-cyclopropyl)-amide;

(2S,4R)-1-[1-(5-Chloro-3-fluoro-pyridin-2-yl)-cyclopropanecarbonyl]-4-[2-chloro-4-(2-methyl-pyridin-3-yl)-benzenesulfonyl]-pyrrolidine-2-carboxylic acid (1-cyano-cyclopropyl)-amide;

(2S,4R)-4-[2-Chloro-4-(2-methyl-pyridin-3-yl)-benzenesulfonyl]-1-[1-(3-fluoro-5-trifluoromethyl-pyridin-2-yl)-cyclopropanecarbonyl]-pyrrolidine-2-carboxylic acid (1-cyano-cyclopropyl)-amide;

(2S,4R)-4-[2-Chloro-4-(2-methyl-pyridin-3-yl)-benzenesulfonyl]-1-[1-(3-fluoro-5-iodo-pyridin-2-yl)-cyclopropanecarbonyl]-pyrrolidine-2-carboxylic acid (1-cyano-cyclopropyl)-amide;

(2S,4R)-4-[2-Chloro-4-(2-methyl-pyridin-3-yl)-benzenesulfonyl]-1-[1-(3,5-dichloro-pyridin-2-yl)-cyclopropanecarbonyl]-pyrrolidine-2-carboxylic acid (1-cyano-cyclopropyl)-amide;

(2S,4R)-4-[2-Chloro-4-(1-methyl-1H-pyrazol-4-yl)-benzenesulfonyl]-1-[1-(3-fluoro-5-iodo-pyridin-2-yl)-cyclopropanecarbonyl]-pyrrolidine-2-carboxylic acid (1-cyano-cyclopropyl)-amide;

(2S,4R)-4-[2-Chloro-4-(1-methyl-1H-pyrazol-4-yl)-benzenesulfonyl]-1-[1-(3-fluoro-5-trifluoromethyl-pyridin-2-yl)-cyclopropanecarbonyl]-pyrrolidine-2-carboxylic acid (1-cyano-cyclopropyl)-amide; or (2S,4R)-4-[2-Chloro-4-(1-methyl-1H-pyrazol-4-yl)-benzenesulfonyl]-1-[1-(3,5-dichloro-pyridin-2-yl)-cyclopropanecarbonyl]-pyrrolidine-2-carboxylic acid (1-cyano-cyclopropyl)-amide, or a pharmaceutically acceptable salt thereof.

15. A process for the preparation of a compound of formula (I) as defined in claim 1, comprising one of the following steps:

(a) The reaction of a compound of formula (A)

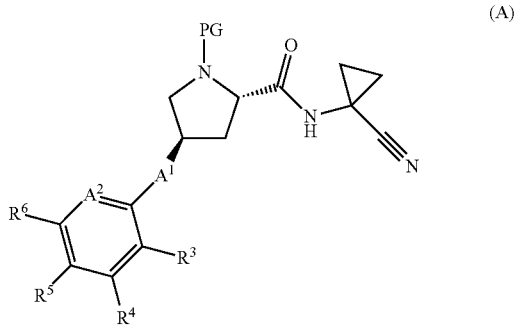

(A)

in the presence of acid, wherein $A^1$, $A^2$ and $R^1$ to $R^6$ are as defined in any one of claims 1 to 12 and wherein PG is an amine protecting group;

(b) The reaction of a compound of formula (B1)

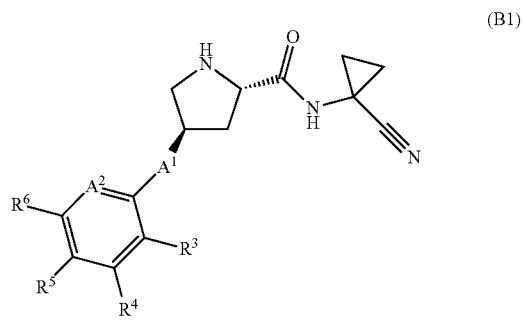

(B1)

with a compound of formula (B2)

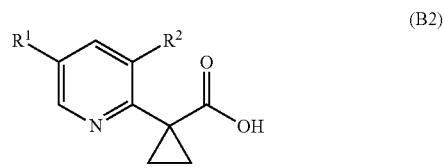

(B2)

in the presence of a base and an amide coupling agent and a base, wherein $A^1$, $A^2$ and $R^1$ to $R^6$ are as defined in any one of claims 1 to 12;

(c) The reaction of a compound of formula (C)

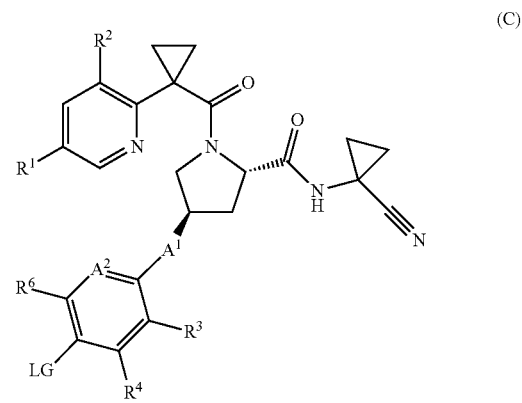

(C)

in the presence of $R^5B(OR)_2$, a base and a Suzuki catalyst, wherein $A^1$, $A^2$ and $R^1$ to $R^4$ and $R^6$ are as defined in any one of claims 1 to 12, LG is a leaving group, $R^5$ is alkylpyridinyl, halopyridinyl or alkylpyrazolyl and R is hydrogen or methyl, or both R, together with the boron atom to which they are attached, form 2,4,4,5,5-pentamethyl-[1,3,2]dioxaborolane; or (d) The reaction of a compound of formula (D)
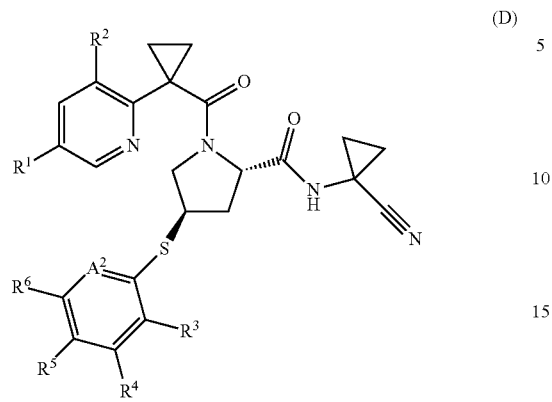
in the presence of an oxidizing agent, wherein $A^1$ and $R^1$ to $R^6$ are as defined in any one of claims 1 to 12.
16. The compound of claim 1, when manufactured according to a process of claim 15.
17. A pharmaceutical composition comprising a compound of any one of claim 1, 13 or 14, and a therapeutically inert carrier.
* * * * *